US010401359B2

(12) United States Patent
Barker et al.

(10) Patent No.: US 10,401,359 B2
(45) Date of Patent: Sep. 3, 2019

(54) METHODS FOR DETECTING AND TREATING FUNGAL INFECTIONS

(71) Applicant: THE TRANSLATIONAL GENOMICS RESEARCH INSTITUTE, Phoenix, AZ (US)

(72) Inventors: Bridget M. Barker, Flagstaff, AZ (US); Patrick Pirrotte, Phoenix, AZ (US)

(73) Assignee: The Translational Genomics Research Institute, Phoenix, AZ (US)

(*) Notice: Subject to any disclaimer, the term of this patent is extended or adjusted under 35 U.S.C. 154(b) by 0 days.

(21) Appl. No.: 15/677,009

(22) Filed: Aug. 14, 2017

(65) Prior Publication Data

US 2018/0106802 A1 Apr. 19, 2018

Related U.S. Application Data

(60) Provisional application No. 62/374,082, filed on Aug. 12, 2016.

(51) Int. Cl.

| | |
|---|---|
| ***A61K 39/002*** | (2006.01) |
| ***G01N 33/569*** | (2006.01) |
| ***G01N 33/68*** | (2006.01) |
| ***A61K 38/00*** | (2006.01) |
| *C07K 16/14* | (2006.01) |

(52) U.S. Cl.

CPC ....... *G01N 33/56961* (2013.01); *A61K 38/00* (2013.01); *G01N 33/6854* (2013.01); *C07K 16/14* (2013.01); *G01N 2333/37* (2013.01); *G01N 2800/26* (2013.01)

(58) Field of Classification Search

None

See application file for complete search history.

(56) References Cited

PUBLICATIONS

Zhou, et al., "IL-12 prevents mortality in mice infected with Histoplasma capsulatum through induction of IFN-gamma," J Immunol, 155:785-795, 1995.

Schelenz, et al., "Cytokine and chemokine responses following pulmonary challenge with Aspergillus fumigatus: obligatory role of TNF-alpha and GM-CSF in neutrophil recruitment," Med Mycol 37:183-194, 1999.

Yeaman, M.R., "Bacterial-platelet interactions: virulence meets host defense," Future Microbiol, 5:471-506, 2010.

Cox, R. A., "Immunosuppression by cell wall antigens of Coccidioides immitis," Rev Infect Dis 10 Suppl 2:S415-418, 1988.

Lewis, et al., "Dust devil: the life and times of the fungus that causes valley Fever," PLoS Pathog 11:e1004762, 2015.

Brown, et al., "Coccidioidomycosis: epidemiology," Clin Epidemiol, 5:185-197, 2013.

Nguyen, et al., "Recent advances in our understanding of the environmental, epidemiological, immunological, and clinical dimensions of coccidioidomycosis," Clin Microbiol Rev, 26:505-525, 2013.

Nesbit, et al., "Immunological characterization of bronchoalveolar lavage fluid in patients with acute pulmonary coccidioidomycosis," J Infect Dis, 208:857-863, 2013.

Ampel, et al., "Mannose-binding lectin serum levels are low in persons with clinically active coccidioidomycosis. Mycopathologia," 167:173-180, 2009.

Cox, et al., "Induction and expression of cell-mediated immune responses in inbred mice infected with Coccidioides immitis," Infect Immun, 56:13-17, 1988.

Magee, et al. "Roles of gamma interferon and interleukin-4 in genetically determined resistance to Coccidioides immitis," Infect Immun, 63:3514-3519, 1995.

Fierer, et al., "Importance of interleukin-10 in genetic susceptibility of mice to Coccidioides immitis," Infect Immun, 66:4397-4402, 1998.

Cain, et al., "Evolution of the primary immune response to Histoplasma capsulatum in murine lung," Infect Immun, 66:1473-1481, 1998.

Gonzalez, et al., "Production of pro-inflammatory cytokines during the early stages of experimental Paracoccidioides brasiliensis infection," Med Mycol, 41:391-399, 2003.

Caffrey, et al., "IL-1alpha signaling is critical for leukocyte recruitment after pulmonary Aspergillus fumigatus challenge," PLoS Pathog 11:e1004625, 2015.

Murdock, et al., "Interleukin-17A enhances host defense against cryptococcal lung infection through effects mediated by leukocyte recruitment, activation, and gamma interferon production," Infect Immun, 82:937-948, 2014.

Burt, et al., "Molecular markers reveal differentiation among isolates of Coccidioides immitis from California, Arizona and Texas," Mol Ecol, 6:781-786, 1997.

Fisher, et al., "Molecular and phenotypic description of *Coccidioides posadasii* sp. nov., previously recognized as the non-California population of Coccidioides immitis," Mycologia, 94:73-84, 2002.

Friedman, et al., "The assay of virulence of Coccidioides in white mice," J Infect Dis, 97:311-316, 1955.

Zimmermann, et al., "Characterization of Coccidioides immitis isolates by restriction fragment length polymorphisms," J Clin Microbiol, 32:3040-3042, 1994.

Shubitz, et al., "Vaccine-induced cellular immune responses differ from innate responses in susceptible and resistant strains of mice infected with Coccidioides posadasii," Infect Immun, 76:5553-5564, 2008.

Chung, et al., "ChIP-seq and in vivo transcriptome analyses of the Aspergillus fumigatus SREBP SrbA reveals a new regulator of the fungal hypoxia response and virulence." PLoS Pathog 10:e1004487, 2014.

Livak, et al., "Analysis of relative gene expression data using real-time quantitative PCR and the 2(-Delta Delta C(T)) Method," Methods, 25:402-408, 2001.

(Continued)

*Primary Examiner* — Jennifer E Graser

(57) ABSTRACT

Methods are provided to detect and treat a fungal infection. The method may include the steps of obtaining a sample from a subject suspected of having a fungal infection, detecting an Uncharacterized Fungal Protein (CIMG_09001/CPSG_01366) in the sample, and determining the presence on the fungal infection if the Uncharacterized Fungal Protein is detected.

11 Claims, 16 Drawing Sheets

Specification includes a Sequence Listing.

(56) References Cited

PUBLICATIONS

Shevchenko, et al., "In-gel digestion for mass spectrometric characterization of proteins and proteomes," Nat Protoc, 1:2856-2860, 2006.
Keller, et al., "Empirical statistical model to estimate the accuracy of peptide identifications made by MS/MS and database search," Anal Chem, 74:5383-5392, 2002.
Bindea, et al., "ClueGO: a Cytoscape plug-in to decipher functionally grouped gene ontology and pathway annotation networks," Bioinformatics, 25:1091-1093, 2009.
Chen, et al., "ToppGene Suite for gene list enrichment analysis and candidate gene prioritization," Nucleic Acids Res, 37:W305-311, 2009.
Cuervo, et al., "Selective degradation of annexins by chaperone-mediated autophagy," J Biol Chem, 275:33329-33335, 2000.
Cowburn, et al., "Aminopeptidase N (CD13) regulates tumor necrosis factor-alpha-induced apoptosis in human neutrophils," J Biol Chem, 281:12458-12467, 2006.
Scharfstein, Julio, "Parasite cysteine proteinase interactions with alpha 2-macroglobulin or kininogens: differential pathways modulating inflammation and innate immunity in infection by pathogenic trypanosomatids," Immunobiology, 211:117-125, 2006.
Merle, et al., "Complement System Part II: Role in Immunity," Front Immunol, 6:257, 2015.
Dutra, et al., "Herne on innate immunity and inflammation," Front Pharmacol, 5:115, 2014.
Vadesz, et al., "Ubiquitination and proteolysis in acute lung injury," Chest, 141:763-771, 2012.
Crosby, et al., "Epithelial repair mechanisms in the lung," Am J Physiol Lung Cell Mol Physio,I 298:L715-731, 2010.
McAleer, et al., "Directing traffic: IL-17 and IL-22 coordinate pulmonary immune defense," Immunol Rev, 260:129-144, 2014.
Parker, et al., "Innate immunity in the respiratory epithelium," Am J Respir Cell Mol Biol, 45:189-201, 2011.
Tang, et al., "Lymphocyte CFTR promotes epithelial bicarbonate secretion for bacterial killing," J Cell Physiol, 227:3887-3894, 2012.
Christin, et al., "Human platelets damage Aspergillus fumigatus hyphae and may supplement killing by neutrophils," Infect Immun, 66:1181-1189, 1998.
Sharpton, et al., "Comparative genomic analyses of the human fungal pathogens Coccidioides and their relatives," Genome Res, 19:1722-1731, 2009.
Pishko, et al., "Isolation and characterization of two chitinase-encoding genes (cts1, cts2) from the fungus Coccidioides immitis," Gene, 167:173-177, 1995.
Whiston, et al., Comparative transcriptomics of the saprobic and parasitic growth phases in *Coccidioides* spp. PLoS One 7:e41034, 2012.
Johnson, et al., "The coccidioidal complement fixation and immunodiffusion-complement fixation antigen is a chitinase," Infect Immun, 60:2588-2592, 1992.
Orsborn, et al., "Protein expression profiling of Coccidioides posadasii by two-dimensional differential in-gel electrophoresis and evaluation of a newly recognized peroxisomal matrix protein as a recombinant vaccine candidate," Infect Immun, 74:1865-1872, 2006.
Sobonya, et al., "Cavitary pulmonary coccidioidomycosis: pathologic and clinical correlates of disease," Hum Pathol, 45:153-159, 2014.
Cox, et al., "Coccidioidomycosis: host response and vaccine development," Clin Microbiol Rev, 17:804-839, 2004.
Check, et al., "Systemic and lung protein changes in sarcoidosis. Lymphocyte counts, gallium uptake values, and serum angiotensin-converting enzyme levels may reflect different aspects of disease activity," Ann N Y Acad Sci, 465:407-417, 1986.
Atochina, et al., "Enhanced lung injury and delayed clearance of Pneumocystis carinii in surfactant protein A-deficient mice: attenuation of cytokine responses and reactive oxygen-nitrogen species," Infect Immun, 72:6002-6011, 2004.
Jin, et al., "Increased claudin-3, -4 and -18 levels in bronchoalveolar lavage fluid reflect severity of acute lung injury," Respirology 18:643-651, 2013.
Muhammed, et al., "Mouse models for the study of fungal pneumonia: a collection of detailed experimental protocols for the study of Coccidioides, Cryptococcus, Fusarium, Histoplasma and combined infection due to Aspergillus-Rhizopus," Virulence, 3:329-338, 2012.
Dixon, et al., "Fungus dose-dependent primary pulmonary aspergillosis in immunosuppressed mice," Infect Immun, 57:1452-1456, 1989.
Sawyer, Richard T., "Experimental pulmonary candidiasis," Mycopathologia, 109:99-109, 1990.
Wormley, et al., "Protection against cryptococcosis by using a murine gamma interferon-producing Cryptococcus neoformans strain," Infect Immun, 75:1453-1462, 2007.
Nicas, et al., "A risk analysis for airborne pathogens with low infectious doses: application to respirator selection against Coccidioides immitis spores," Risk Anal, 22:1153-1163, 2002.
Cox, et al., "Suppression of T-lymphocyte response by Coccidioides immitis antigen," Infect Immun, 56:1424-1429, 1988.
Hung, et al., "A major cell surface antigen of Coccidioides immitis which elicits both humoral and cellular immune responses," Infect Immun, 68:584-593, 2000.
Hung, et al., "A parasitic phase-specific adhesin of Coccidioides immitis contributes to the virulence of this respiratory fungal pathogen," Infect Immun, 70:3443-3456, 2002.
Hung, et al., "A metalloproteinase of Coccidioides posadasii contributes to evasion of host detection," Infect Immun, 73:6689-6703, 2005.
Johannesson, et al., "Concerted evolution in the repeats of an immunomodulating cell surface protein, SOWgp, of the human pathogenic fungi Coccidioides immitis and C. posadasii," Genetics, 171:109-117, 2005.
Hung, et. al., "Virulence mechanisms of Coccidioides," Ann N Y Acad Sci 1111:225-235, 2007.
Deitsch, et al., "Common strategies for antigenic variation by bacterial, fungal and protozoan pathogens," Nat Rev Microbiol, 7:493-503, 2009.
Chotirmall, et al., "Immunoevasive Aspergillus virulence factors," Mycopathologia, 178:363-370, 2014.
Reddick, et al., "Bacteria fighting back: how pathogens target and subvert the host innate immune system," Mol Cell, 54:321-328, 2014.
Neafsey, et al., "Population genomic sequencing of Coccidioides fungi reveals recent hybridization and transposon control," Genome Res, 20:938-946, 2010.

```
                              SEQUENCE LISTING


<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Primer Sequence

<400> SEQUENCE: 1

accaactgtc ttgctccttt g                                               21


<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2

agtcttctga gtggcggtat ag                                              22


<210> SEQ ID NO 3
<211> LENGTH: 116
<212> TYPE: PRT
<213> ORGANISM: Artificial Sequence
<220> FEATURE:
<223> OTHER INFORMATION: CIMG_09001

<400> SEQUENCE: 3

Met His Val Leu Ser Ala Val Thr Val Ala Leu Ala Ala Phe Ser Ser
1               5                   10                  15

Ser Thr Leu Ala Ala Ile Cys His His Glu Ala Lys Gly Glu Asn Cys
            20                  25                  30

Met Ser Lys Asp Asp Ala Lys Arg Ala Val Ala Ala Tyr Cys Arg Gly
        35                  40                  45

His Phe His Arg Lys Cys Val Ser Trp Lys Lys Val Glu Gly Thr Glu
    50                  55                  60

Gly Gly Val Gly Tyr Val Ala Gln Asn Gly Lys Phe Lys Asn Glu Asp
65                  70                  75                  80

Leu Cys Val Lys Ala Gly Leu Leu Ile Val Glu Gln Cys Tyr Gly Ile
                85                  90                  95

Ala Ala Gly Gly Ser Arg Thr Arg Arg Phe Ser Ala Leu Asp Phe Arg
            100                 105                 110

Tyr Cys Glu Trp
        115
```

METHODS FOR DETECTING AND TREATING FUNGAL INFECTIONS

CROSS REFERENCE TO RELATED APPLICATIONS

The present application claims priority to U.S. Provisional Application Ser. No. 62/374,082 filed on Aug. 12, 2016, the contents of which is hereby incorporated by reference in its entirety.

STATEMENT REGARDING FEDERALLY SPONSORED RESEARCH

This invention was made with government support under K22 AI104801 awarded by the National Institute of Allergy and Infectious Diseases. The government has certain rights in this invention.

FIELD

The present invention relates to the field of methods of diagnosing and treating fungal infections, and more specifically, to diagnosing and treating Valley Fever.

BACKGROUND

Coccidioidomycosis, more commonly known as Valley Fever, is a fungal infection caused by inhaling either *Coccidioides immitis* or *Coccidioides posadasii* conidia that are found in the soil in arid to semi-arid regions of the Americas. Both *Coccidioides* species, *Coccidioides immitis* and *Coccidioides posadasii*, share an asexual life cycle characterized by two stages, the saprobic cycle and the parasitic cycle. The saprobic cycle is found in the environment. During the saprobic cycle, these fungi alternate between two main cell types in the environment: arthroconidia and hyphae. The arthroconidial phase is believed to be the major infectious particle found in the environment. When a susceptible host inhales an arthroconidium, the parasitic cycle begins. The parasitic life cycle is initiated when arthroconidia enlarge and transform into immature spherules. Spherules undergo free nuclear division and begin developing endospores. During an active parasitic cycle, an arthroconidium can transition to a mature rupturing spherule within five days after the initial exposure (see Reference 1). Once the spherule ruptures and releases endospores, each endospore can develop into a new spherule and the parasitic cycle can continue growing exponentially.

It is estimated that 40% of human *Coccidioides* infections are symptomatic (see Reference 2). Acute or chronic pulmonary disease is most common manifestation, however disseminated disease occurs in approximately 1% of *Coccidioides* infections (see Reference 2). Certain factors such as African or Filipino ancestry, immunosuppression, pregnancy, and male gender increase the risk of a disseminated infection (see References 2 and 3). The remaining 60% of human *Coccidioides* infections are asymptomatic and generally result in clearance or development of asymptomatic lung nodules. Morphological variation is highest during early days of infection, when the inhaled environmental conidia are switching to the parasitic lifestyle.

SUMMARY

A need exists for methods of characterizing the innate immune response in the first five days of *Coccidioides* infection, diagnostic methods for detecting *Coccidioides*, particularly during the onset of *Coccidioides* infection, and treatment methods based on the host immune response early in infection. In the present disclosure, various methods are employed to examine and characterize the early host response to *Coccidioides* infection in a BALB/c mouse model of pulmonary coccidioidomycosis at time points not previously characterized. Methods are provided to detect and treat a fungal infection.

In various embodiments, the method may include the steps of obtaining a sample from a subject suspected of having a fungal infection, detecting an Uncharacterized Fungal Protein (CIMG_09001/CPSG_01366) in the sample, and determining the presence on the fungal infection if the Uncharacterized Fungal Protein is detected.

The fungal infection may be caused by a species of *Coccidioides*. The Uncharacterized Fungal Protein may be detected using liquid chromatography. The Uncharacterized Fungal Protein may be detected using an antibody. The sample may be a pulmonary sample. The sample may be obtained within one week of the subject being exposed to the fungal infection.

A method of treating a fungal infection may comprise the step of augmenting an expression level or functionality of an Uncharacterized Fungal Protein (CIMG_09001/CPSG_01366). The step of augmenting the expression level may comprise reducing the expression level of the Uncharacterized Fungal Protein. The step of augmenting the expression level may comprise increasing the expression level of the Uncharacterized Fungal Protein. The step of augmenting the functionality may comprise inhibiting the functionality of the Uncharacterized Fungal Protein. Inhibition of the functionality of the Uncharacterized Fungal Protein may be achieved by the administration of one of a small molecule, a biologic, or interfering RNA.

A method of treating a fungal infection may comprise the steps of obtaining a sample from a subject suspected of having a fungal infection, detecting an Uncharacterized Fungal Protein (CIMG_09001/CPSG_01366) in the sample, and augmenting an expression level or functionality of an Uncharacterized Fungal Protein (CIMG_09001/CPSG_01366).

The foregoing features and elements may be combined in various combinations without exclusivity, unless expressly indicated otherwise. These features and elements as well as the operation thereof will become more apparent in light of the following description. It should be understood, however, the following description is intended to be exemplary in nature and non-limiting.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the figures, wherein like numerals may denote like elements.

DETAILED DESCRIPTION

Figure 1A:
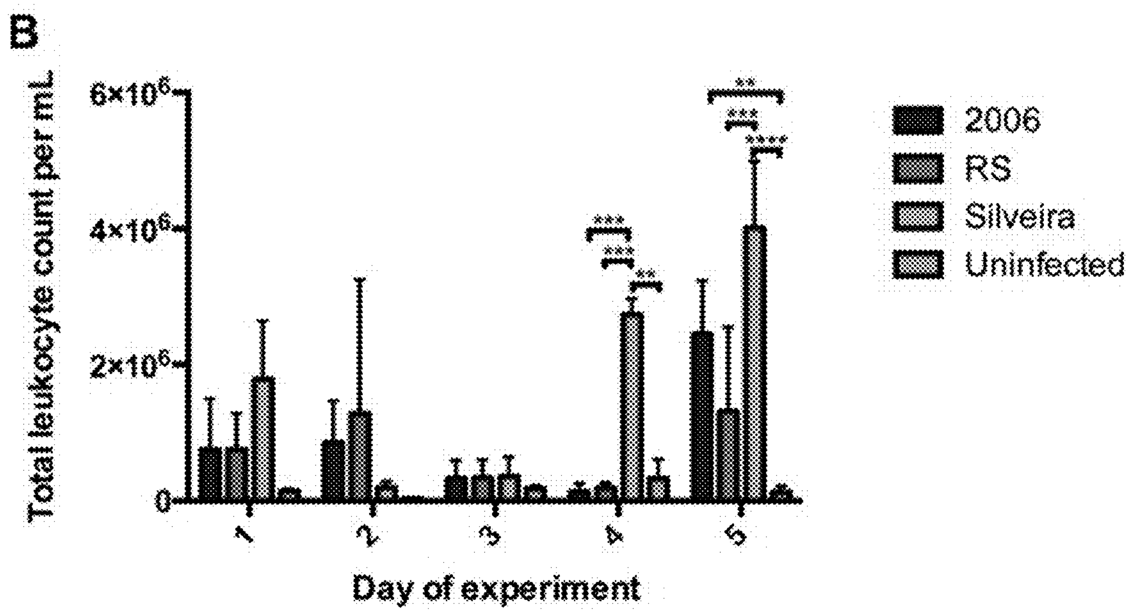
FIGS. 1A and 1B illustrate results of the detection of *Coccidioides* infection in BALB/c mice.

It is to be understood that unless specifically stated otherwise, references to "a," "an," and/or "the" may include one or more than one and that reference to an item in the singular may also include the item in the plural. Reference to an element by the indefinite article "a," "an" and/or "the" does not exclude the possibility that more than one of the elements are present, unless the context clearly requires that there is one and only one of the elements. As used herein, the term "comprise," and conjugations or any other variation thereof, are used in its non-limiting sense to mean that items following the word are included, but items not specifically mentioned are not excluded.

As used herein, "amplification reaction" refers to a method of detecting target nucleic acid by in vitro amplification of DNA or RNA.

As used herein, "polymerase chain reaction (PCR)" refers to the amplification of a specific DNA sequence, termed target or template sequence, that is present in a mixture, by adding two or more short oligonucleotides, also called primers, that are specific for the terminal or outer limits of the template sequence. The template-primers mixture is subjected to repeated cycles of heating to separate (melt) the double-stranded DNA and cooling in the presence of nucleotides and DNA polymerase such that the template sequence is copied at each cycle.

The term "primer" refers to DNA oligonucleotides complementary to a region of DNA and serves as the initiation of amplification reaction from the 5' to 3' direction. For example, a forward and a reverse marker-specific primer can be designed to amplify the marker from a nucleic acid sample.

The term "primer pair" refers to the forward and reverse primers in an amplification reaction leading to amplification of a double-stranded DNA region of the target.

The term "target" refers to a nucleic acid region bound by a primer pair that is amplified through an amplification reaction. The PCR "product" or "amplicon" is the amplified nucleic acid resulting from PCR of a set of primer pairs.

The term "multiplex amplification reaction" herein refers to the detection of more than one template in a mixture by the addition of more than one set of oligonucleotide primers.

"Amplification" is a special case of nucleic acid replication involving template specificity. Amplification may be a template-specific replication or a non-template-specific replication (i.e., replication may be specific template-dependent or not). Template specificity is here distinguished from fidelity of replication (synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out. The amplification process may result in the production of one or more amplicons.

The term "template" refers to nucleic acid originating from a sample that is analyzed for the presence of one or more markers. In contrast, "background template" or "control" is used in reference to nucleic acid other than sample template that may or may not be present in a sample. Background template is most often inadvertent. It may be the result of carryover, or it may be due to the presence of nucleic acid contaminants sought to be purified out of the sample. For example, nucleic acids from organisms other than those to be detected may be present as background in a test sample.

The term "amplifiable nucleic acid" refers to nucleic acids that may be amplified by any amplification method. It is contemplated that "amplifiable nucleic acid" will usually comprise "sample template." The terms "PCR product," "PCR fragment," "amplification product," and "amplicon" refer to the resultant mixture of compounds after two or more cycles of the PCR steps of denaturation, annealing and extension. These terms encompass the case where there has been amplification of one or more segments of one or more target sequences.

Detection according to some embodiments of the disclosure may comprise contacting the amplified nucleic acid with a probe; and detecting the hybridization of probe with the amplified nucleic acid. Detection may be performed by a variety of methods, such as but not limited to, by a nucleic acid amplification reaction. In some embodiments the amplification reaction maybe an end-point determination or the amplification reaction maybe quantitative. The quantification may be a real-time PCR method. In some embodiments, the real-time PCR may be a SYBR® Green Assay or a TAQMAN® Assay. Detection, in various embodiments, maybe performed by hybridization using probes specific to target sequences. According to various embodiments, combinations of amplification and hybridization may be used for detection.

As used herein, "real-time PCR" may refer to the detection and quantitation of a DNA or a surrogate thereof in a sample.

The disclosure encompasses assessing the expression of a marker expressed by a host organism having a *Coccidioides* infection in order to identify the *Coccidioides* infection based on expression of the marker. Assessing the expression may comprise detecting the presence of an uncharacterized protein, including an uncharacterized fungal protein (CIMG_09001/CPSG_01366). The method may be used to assess the expression of uncharacterized fungal protein (CIMG_09001/CPSG_01366) as a marker. The methods may involve receiving a sample from a subject, adding a first reagent specific to uncharacterized fungal protein (CIMG_09001/CPSG_01366) (alone or in combination with another marker) to a mixture that comprises the sample, and subjecting the mixture to conditions that allow detection of the binding of the reagent. The methods may be used to assess the expression of uncharacterized fungal protein (CIMG_09001/CPSG_01366) protein as a marker. The first reagent may comprise a first antibody. The methods may also be used to assess the expression of uncharacterized fungal protein (CIMG_09001/CPSG_01366) mRNA or cDNA as a marker. In this case, the first reagent comprises a first nucleic acid. The first nucleic acid may be any nucleic acid capable of binding to uncharacterized fungal protein (CIMG_09001/CPSG_01366) sequence (Accession XP_001239380.2; SEQ ID NO: 3-mhvlsavtva laafssstla aichheakge ncmskddakr avaaycrghf hrkcvswkkv egteggv-gyv aqngkfkned lcvkaglliv eqcygiaagg srtrrfsald frycew).

A marker may be any molecular structure produced by a cell, expressed inside the cell, accessible on the cell surface, or secreted by the cell. A marker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination. A marker may also be called a target and the terms are used interchangeably.

A marker may be represented by the sequence of a nucleic acid from which it can be derived or any other chemical structure. Examples of such nucleic acids include miRNA, tRNA, siRNA, mRNA, cDNA, or genomic DNA sequences including complimentary sequences. Alternatively, a marker may be represented by a protein sequence. The concept of a marker is not limited to the products of the exact nucleic acid sequence or protein sequence by which it may be represented. Rather, a marker encompasses all molecules that may be detected by a method of assessing the expression of the marker.

Expression encompasses any and all processes through which material derived from a nucleic acid template may be produced. Expression thus includes processes such as RNA transcription, mRNA splicing, protein translation, protein folding, post-translational modification, membrane transport, associations with other molecules, addition of carbohydrate moeties to proteins, phosphorylation, protein complex formation and any other process along a continuum that results in biological material derived from genetic material whether in vitro, in vivo, or ex vivo. Expression also encompasses all processes through which the production of material derived from a nucleic acid template may be actively or passively suppressed. Such processes include all aspects of transcriptional and translational regulation. Examples include heterochromatic silencing, transcription factor inhibition, any form of RNAi silencing, microRNA silencing, alternative splicing, protease digestion, posttranslational modification, and alternative protein folding.

Expression may be assessed by any number of methods used to detect material derived from a nucleic acid template used currently in the art and yet to be developed. Examples of such methods include any nucleic acid detection method including the following nonlimiting examples, microarray analysis, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, direct sequencing of genomic DNA, or any other method of detecting a specific nucleic acid now known or yet to be disclosed. Other examples include any process of assessing protein expression including flow cytometry, immunohistochemistry, ELISA, Western blot, and immunoaffinity chromatograpy, HPLC, mass spectrometry, protein microarray analysis, PAGE analysis, isoelectric focusing, 2-D gel electrophoresis, or any enzymatic assay.

The present disclosure relates to methods of diagnosing and treating fungal infections, and more specifically, Coccidioidomycosis, commonly referred to as Valley Fever. *Coccidioides immitis* and *C. posadasii* are soil-dwelling fungi and the causative agents of coccidioidomycosis, a mycosis endemic to certain semi-arid regions within the Americas. The most common route of infection is by inhalation of airborne *Coccidioides* arthroconidia. Once a susceptible host inhales the conidia, a transition into mature endosporulated spherules can occur within the first five days of infection.

Other methods used to assess expression include the use of natural or artificial ligands capable of specifically binding a marker. Such ligands include antibodies, antibody complexes, conjugates, natural ligands, small molecules, nanoparticles, or any other molecular entity capable of specific binding to a marker. Antibodies may be monoclonal, polyclonal, or any antibody fragment including an Fab, F(ab)2, Fv, scFv, phage display antibody, peptibody, multispecific ligand, or any other reagent with specific binding to a marker. Ligands may be associated with a label such as a radioactive isotope or chelate thereof, dye (fluorescent or nonfluorescent) stain, enzyme, metal, or any other substance capable of aiding a machine or a human eye from differentiating a cell expressing a marker from a cell not expressing a marker. Additionally, expression may be assessed by monomeric or multimeric ligands associated with substances capable of killing the cell. Such substances include protein or small molecule toxins, cytokines, pro-apoptotic substances, pore forming substances, radioactive isotopes, or any other substance capable of killing a cell.

Differential expression encompasses any detectable difference between the expression of a marker in one sample relative to the expression of the marker in another sample. Differential expression may be assessed by a detector, an instrument containing a detector, or by aided or unaided human eye. Examples include but are not limited to differential staining of cells in an assay configured to detect a marker, differential detection of bound RNA on a microarray to which a sequence capable of binding to the marker is bound, differential results in measuring RT-PCR measured in Ct or alternatively in the number of PCR cycles necessary to reach a particular optical density at a wavelength at which a double stranded DNA binding dye (e.g. SYBR Green) incorporates, differential results in measuring label from a reporter probe used in a real-time RT-PCR reaction, differential detection of fluorescence on cells using a flow cytometer, differential intensities of bands in a Northern blot, differential intensities of bands in an RNAse protection assay, differential cell death measured by apoptotic markers, differential cell death measured by shrinkage of a tumor, or any method that allows a detection of a difference in signal between one sample or set of samples and another sample or set of samples.

The expression of the marker in a sample may be compared to a level of expression predetermined to predict the presence or absence of a particular physiological characteristic. The level of expression may be derived from a single control or a set of controls. control may be any sample with a previously determined level of expression. control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources. Comparison of the expression of the marker in the sample to a particular level of expression results in a prediction that the sample exhibits or does not exhibit the cellular or physiological characteristic.

Prediction of a cellular or physiological characteristic includes the prediction of any cellular or physiological state that may be predicted by assessing the expression of a marker. Examples include but are not limited to the likelihood that one or more diseases is present or absent, the likelihood that a present disease will progress, remain unchanged, or regress, the degree to which a disease will respond or not respond to a particular therapy. Further examples include the likelihood that a cell will move, senesce, apoptose, differentiate, metastasize, or change from any state to any other state or maintain its current state.

Expression of a marker in a sample may be more or less than that of a level predetermined to predict the presence or absence of a cellular or physiological characteristic. The expression of the marker in the sample may be more than 1,000,000×, more than 100,000×, more than 10,000×, more than 1000×, more than 100×, more than 10×, more than 5×, more than 2×, about 1×, more than 0.5×, more than 0.1× more than 0.01×, more than 0.001×, more than 0.0001×, more than 0.00001×, more than 0.000001×, more than 0.0000001× or less than 0.0000001× that of a level predetermined to predict the presence or absence of a cellular or physiological characteristic.

The disclosure contemplates assessing the expression of the marker in any biological sample from which the expression may be assessed. One skilled in the art would know to select a particular biological sample and how to collect said sample depending upon the marker that is being assessed. Examples of sources of samples include but are not limited to biopsy or other in vivo or ex vivo analysis of prostate, breast, skin, muscle, facia, brain, endometrium, lung, head and neck, pancreas, small intestine, blood, liver, testes, ovaries, colon, skin, stomach, esophagus, spleen, lymph node, bone marrow, kidney, placenta, or fetus. In some aspects of the disclosure, the sample comprises a fluid sample, such as peripheral blood, lymph fluid, ascites, serous fluid, pleural effusion, sputum, cerebrospinal fluid, amniotic fluid, lacrimal fluid, stool, or urine. Samples include single cells, whole organs or any fraction of a whole organ, in any condition including in vitro, ex vivo, in vivo, post-mortem, fresh, fixed, or frozen.

One type of cellular or physiological characteristic is the risk that a particular disease outcome will occur. Assessing this risk includes the performing of any type of test, assay, examination, result, readout, or interpretation that correlates with an increased or decreased probability that an individual has had, currently has, or will develop a particular disease, disorder, symptom, syndrome, or any condition related to health or bodily state. Examples of disease outcomes include, but need not be limited to survival, death, progression of existing disease, remission of existing disease, initiation of onset of a disease in an otherwise disease-free subject, or the continued lack of disease in a subject in which there has been a remission of disease. Assessing the risk of a particular disease encompasses diagnosis in which the type of disease afflicting a subject is determined. Assessing the risk of a disease outcome also encompasses the concept of prognosis. A prognosis may be any assessment of the risk of disease outcome in an individual in which a particular disease has been diagnosed. Assessing the risk further encompasses prediction of therapeutic response in which a treatment regimen is chosen based on the assessment. Assessing the risk also encompasses a prediction of overall survival after diagnosis.

Determining the level of expression that signifies a physiological or cellular characteristic may be assessed by any of a number of methods. The skilled artisan will understand that numerous methods may be used to select a level of expression for a particular marker or a plurality of markers that signifies a particular physiological or cellular characteristic. In diagnosing the presence of a disease, a threshold value may be obtained by performing the assay method on samples obtained from a population of patients having a certain type of disease (fungal infection for example) and from a second population of subjects that do not have the disease. In assessing disease outcome or the effect of treatment, a population of patients, all of which have, a disease such as a fungal infection, may be followed for a period of time. After the period of time expires, the population may be divided into two or more groups. For example, the population may be divided into a first group of patients whose disease progresses to a particular endpoint and a second group of patients whose disease does not progress to the particular endpoint. Examples of endpoints include disease recurrence, death, metastasis or other states to which disease may progress. If expression of the marker in a sample is more similar to the predetermined expression of the marker in one group relative to the other group, the sample may be assigned a risk of having the same outcome as the patient group to which it is more similar.

In addition, one or more levels of expression of the marker may be selected that provide an acceptable ability of its ability to signify a particular physiological or cellular characteristic. Examples of such characteristics include identifying or diagnosing a particular disease, assessing a risk of outcome or a prognostic risk, or assessing the risk that a particular treatment will or will not be effective. A subject includes any human or non-human mammal, including for example: a primate, cow, horse, pig, sheep, goat, dog, cat, or rodent, capable of developing cancer including human patients that are suspected of having a fungal infection, that have been diagnosed with a fungal infection, or that have been or are suspected to have exposed to a fungus.

Some embodiments of the invention may comprise the use of one or more methods of amplifying a nucleic acid-based starting material (i.e., a template, including genomic DNA, crude DNA extract, single-stranded DNA, double-stranded DNA, cDNA, RNA, or any other single-stranded or double-stranded nucleic acids). Nucleic acids may be selectively and specifically amplified from a template nucleic acid contained in a sample. In some nucleic acid amplification methods, the copies are generated exponentially. Examples of nucleic acid amplification methods known in the art include: polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as φ29, whole genome PCR, in vitro transcription with T7 RNA polymerase or any other RNA polymerase, or any other method by which copies of a desired sequence are generated.

In addition to genomic DNA, any polynucleotide sequence can be amplified with an appropriate set of primer molecules. In particular, the amplified segments created by the PCR process itself are, themselves, efficient templates for subsequent PCR amplifications.

PCR generally involves the mixing of a nucleic acid sample, two or more primers or oligonucleotides (primers and oligonucleotides are used interchangeably herein) that are designed to recognize the template DNA, a DNA polymerase, which may be a thermostable DNA polymerase such as Taq or Pfu, and deoxyribose nucleoside triphosphates (dNTP's). In some embodiments, the DNA polymerase used can comprise a high fidelity Taq polymerase such that the error rate of incorrect incorporation of dNTPs is less than one per 1,000 base pairs. Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example 40-75° C.). In real-time PCR analysis, additional reagents, methods, optical detection systems, and devices known in the art are used that allow a measurement of the magnitude of fluorescence in proportion to concentration of amplified template. In such analyses, incorporation of fluorescent dye into the amplified strands may be detected or measured.

Either primers or primers along with probes allow a quantification of the amount of specific template DNA present in the initial sample. In addition, RNA may be detected by PCR analysis by first creating a DNA template from RNA through a reverse transcriptase enzyme (i.e., the creation of cDNA). The marker expression may be detected by quantitative PCR analysis facilitating genotyping analysis of the samples.

In some forms of PCR assays, quantification of a target in an unknown sample is often required. Such quantification may be determined in reference to the quantity of a control sample. The control sample starting material/template may be co-amplified in the same tube in a multiplex assay or may be amplified in a separate tube. Generally, the control sample contains template at a known concentration. The control sample template may be a plasmid construct comprising only one copy of the amplification region to be used as quantification reference. To calculate the quantity of a target in an unknown sample, various mathematical models are established. Calculations are based on the comparison of the distinct cycle determined by various methods, e.g., crossing points (CP) and cycle threshold values (Ct) at a constant level of fluorescence; or CP acquisition according to established mathematic algorithm.

Some embodiments of the invention may comprise a multiplex assay. As used herein, the term "multiplex" refers to the production of more than one amplicon, PCR product, PCR fragment, amplification product, etc. in a single reaction vessel. In other words, multiplex is to be construed as the amplification of more than one marker-specific sequences within a PCR reaction or assay within the same PCR assay mixture (e.g., more than one amplicon is produced within a single vessel that contains all of the reagents necessary to perform a PCR reaction). In some embodiments, a step prior to performing the PCR (or RT-PCR, quantitative RT-PCR, etc.) reaction can occur such that sets of primers and/or primers and probes are designed, produced, and optimized within a given set of reaction conditions to ensure proper amplicon production during the performance of the PCR.

The algorithm for Ct values in real time-PCR calculates the cycle at which each PCR amplification reaches a significant threshold. The calculated Ct value is proportional to the number of marker copies present in the sample, and the Ct value is a precise quantitative measurement of the copies of the marker found in any sample. In other words, Ct values represent the presence of respective marker that the primer sets are designed to recognize. If the marker is missing in a sample, there should be no amplification in the Real Time-PCR reaction.

Alternatively, the Cp value may be utilized. A Cp value represents the cycle at which the increase of fluorescence is highest and where the logarithmic phase of a PCR begins. For example, the LIGHTCYCLER® 480 Software calculates the second derivatives of entire amplification curves and determines where this value is at its maximum. By using the second-derivative algorithm, data obtained are more reliable and reproducible, even if fluorescence is relatively low.

The various and non-limiting embodiments of the PCR-based method detecting marker expression level as described herein may comprise one or more probes and/or primers. Generally, the probe or primer contains a sequence complementary to a sequence specific to a region of the nucleic acid of the marker gene. A sequence having less than 60% 70%, 80%, 90%, 95%, 99% or 100% identity to the identified gene sequence may also be used for probe or primer design if it is capable of binding to its complementary sequence of the desired target sequence in marker nucleic acid.

Some embodiments of the invention may include a method of comparing a marker in a sample relative to one or more control samples. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources.

In some embodiments, sample or biological sample may include a bodily tissue, fluid, or any other specimen that may be obtained from a living organism that may comprise additional living organisms. By way of example only, in some embodiments, sample or biological sample may include a specimen from a first organism (e.g., a human) that may further comprise an additional organism (e.g., bacteria, including pathogenic or non-pathogenic/commensal bacteria, viruses, parasites, fungi, including pathogenic or non-pathogenic fungi, etc.). In some embodiments of the invention, the additional organism may be separately cultured after isolation of the sample to provide additional starting materials for downstream analyses. In some embodiments, the sample or biological sample may comprise a direct portion of the additional, non-human organism and the host organism (e.g., a biopsy or sputum sample that contains human cells and fungi).

The innate immune and cytokine profile response to coccidioidomycosis has been assessed in a few specific studies. Increases in interferon gamma (IFNγ), tumor necrosis factor alpha (TNFα), and interleukin (IL)-17 in mononuclear cells from bronchoalveolar lavage fluid (BALF) and in peripheral blood mononuclear cells collected from patients with acute pulmonary coccidioidomycosis have been identified (see Reference 4). A significant association between lower mannose-binding lectin serum levels in patients with active coccidioidomycosis compared to uninfected healthy subjects has been described (see Reference 5). Comparing BALB/c and DBA/2 mouse models of coccidioidomycosis, a greater susceptibility to pulmonary *Coccidioides* infection in BALB/c mice due to the development of anergy on day 15 post-infection has been reported (see Reference 6). An acquired suppression of cell-mediated immune reactivity not specific to *Coccidioides* antigens was also discovered in BALB/c mice (see Reference 6). In a subsequent study on intranasal infection challenge of 20 arthroconidia of strain Silveira, it was shown that the more resistant DBA/2 mice mounted an IFNγ driven response, whereas the more susceptible BALB/c mice manifested a predominant IL-4 response to an infection challenge (see Reference 7). Expression of these cytokines was measured at three-day intervals over a 15-day post-infection study, starting on day three (see Reference 7). Increases in IFNγ and IL-4 were not detected until 12 and 9 days respectively post-infection. Further investigation comparing intraperitoneal infection in four inbred mouse strains on days 7 and 14 post-infection indicated non-protective IL-10 and IL-4 responses to strain RS *Coccidioides* infections in susceptible C57BL/6 mice (see Reference 8).

The cytokine response to challenge infections of other human fungal respiratory pathogens has also been examined in murine models of disease. For example, increased transcription of genes that encode IL-2, IL-4, IL-12, and IFNγ was detected as early as day three post-infection in the lungs of C57BL/6 mice challenged with *Histoplasma capsulatum* (See Reference 9). IFNγ is necessary for control of *H. capsulatum* infection in mice (see Reference 10). Elevated levels of TNFα, IL-6, IL-1β, and macrophage inflammatory protein (MIP) were detected during the first 4 days post infection in BALB/c mice infected with *Paracoccidioides brasiliensis* (see Reference 11). Cytokines TNFα and IL-1α have been shown to be important for leukocyte recruitment and control of infection of the pathogen *Aspergillus fumigatus* in mice (see References 12 and 13). When examining *Cryptococcus neoformans* in a C57BL/6 mouse model of infection, IL-17α increase is mediated by leukocyte recruitment and activation and IFNγ production after intratracheal challenge (see Reference 14).

In the present disclosure, the host response in a murine model of coccidioidomycosis was examined during a time-period of infection that has not previously been well characterized, i.e., by examining the first five days of infection in a BALB/c mouse model of infection, when the morphological shift from the saprobic to parasitic cycle occurs. To examine the infection dynamics of *Coccidioides*, cytokine expression profile at the onset of infection was studied herein. Lung tissue and bronchoalveolar lavage fluids (BALF) was collected from BALB/c mice that were infected with a *C. immitis* pure strain, a *C. immitis* hybrid strain, or a *C. posadasii* strain as well as uninfected mice. The expression profiles of selected cytokines were assessed by real-time reverse transcription (RT)-PCR of RNA extracted from the mouse lung tissues and a multiplex bead array for proteins present in BALFs. Finally, protein expression profiles from BALFs during day five post-infection were determined using mass spectrometry to identify potential host biomarkers and fungal proteins expressed during pulmonary coccidioidomycosis. The host response was compared to each of the *Coccidioides* strains used by assessing the level of transcription of select cytokine genes in lung tissues and characterized host and fungal proteins present in BALF.

The following examples are given for purely illustrative and non-limiting purposes of the present invention.

EXAMPLE

For this study, the immune response was analyzed for mice intranasally infected with arthroconidia from human clinical isolates of *Coccidioides*: a *C. immitis* pure isolate (hereinafter "2006"), a *C. immitis* hybrid isolate (hereinafter "RS"), and a *C. posadasii* pure isolate (hereinafter "Silveira"). It was initially anticipated that the three *Coccidioides* spp. isolates would have comparable overall inflammatory response and infection kinetics. In contrast to the expectation, there appeared to be significant differential responses among the isolates used in this study. It was discovered that of the three *Coccidioides* isolates that were used in this study, the *C. posadasii* isolate Silveira appeared to cause the highest relative fungal burden in mouse lung tissue. The *C. posadasii* isolate Silveira also caused a significantly higher influx of leukocytes as soon as day four of infection that was not observed in the other infection groups on that day. By day five of infection, a significant increase in leukocytes was present for all infection groups. A differential host response to the three *Coccidioides* isolates was also observed when examining host cytokine gene mRNA levels in lung tissue. A differential and diverse cytokine gene expression profile was associated with each *Coccidioides* isolate.

Mouse Inoculations

*Coccidioides immitis* isolate 2006 (see Reference 15), *C. immitis* hybrid isolate RS (see Reference 16), and *C. posadasii* isolate Silveira were used in this study. Female 6-8 week old BALB/c mice were anesthetized with ketamine/xylene and intranasally inoculated with 100,000 arthroconidia suspended in 30 μL phosphate buffered saline (PBS) (see Reference 19). Control mice were inoculated with PBS alone. The mice were housed according to NIH guidelines in a biosafety level 3 animal laboratory. All procedures were approved by the Institutional Animal Care and Use Committee for the University of Arizona.

Three mice from each infection group (2006, RS, Silveira) and two mice from the uninfected group were sacrificed each day post-infection during this five-day study. The lungs were rinsed with 2 mL of phosphate buffered saline with 0.01 mM ethylenediaminetetraacetic acid (EDTA) to collect bronchoalveolar lavage fluids (BALFs). The right lobe of lung was harvested and flash frozen in liquid nitrogen. One milliliter (mL) of each BALF sample was formalin-fixed and underwent a complete cell count using a hemocytometer. The remainder of each BALF sample was filtered and used to quantify protein concentrations.

A total leukocyte count was made from cells present in the BALFs to confirm that the mice mounted an inflammatory response to infection.

FIG. 1A shows the total leukocyte count per mL of collected BALFs by hemocytometer. Error bars indicate standard error from biological replicates (n=3 for each infection group, n=2 for the uninfected group). P-values were calculated using two-way ANOVA followed by Tukey's multiple comparison test. A p-value of less than (<) 0.05 was considered statistically significant and levels of significance are indicated in FIG. 1A by asterisks. A single asterisk (*) indicates a p-value of greater than or equal to 0.05 ($p \geq 0.05$); two asterisks () indicates $p \geq 0.01$; three asterisks (*) indicates $p \geq 0.001$; and four asterisks (****) indicates $p \geq 0.0001$.

Non-statistically significant increases were observed for all infection groups when compared to the uninfected mice on the first day of infection. On day two of infection, the 2006 and RS infection groups had non-statistically significant increases of total leukocyte counts compared to the Silveira infection group and uninfected control group. On day three of infection, all of the three infection groups had comparable leukocyte counts to the uninfected control group. On day four, however, the Silveira infection group had statistically significant higher number of total leukocytes when compared to the 2006 infection group ($p \leq 0.001$), RS infection group ($p \leq 0.001$), and uninfected control group ($p \leq 0.01$). On day five, all infection groups had an increased number of leukocytes counts per mL of BALF than uninfected mice. In agreement with days 1, 3 and 4, the Silveira infection group had the highest number of leukocytes per mL of BALF on average. During necropsy, it was observed that mice infected with the *C. posadasii* isolate Silveira suffered from more severe lung damage starting at day three of infection than the mice infected with *C. immitis* isolate RS and *C. immitis* isolate 2006.

TABLE 1 shows a total leukocyte count made from cells present in the BALFs.

TABLE 1

Summary statistics for total leukocyte counts per mL of BALFs
Mean number of total leukocyte counts per mL[a]

| Isolate | Day 1 | Day 2 | Day 3 | Day 4 | Day 5 |
|---|---|---|---|---|---|
| 2006 [n = 3][b] | 7.53E+05 (0-2.61E+06) | 8.58E+05 (0-2.37E+06) | 3.27E+05 (0-1.0E+06) | 1.25E+05 (0-4.4E+05) | 2.45E+06 (4.95E+05-4.40E+06) |
| RS [n = 3] | 7.50E+05 (0-2.06E+06) | 1.27E+06 (0-6.18E+06) | 3.35E+05 (0-1.01E+06) | 1.85E+05 (0-3.80E+05) | 1.31E+06 (0-4.38E+06) |
| Silveira [n = 3] | 1.78E+06 (0-3.92E+06) | 1.92E+05 (0-4.17E+05) | 3.53E+05 (0-1.10E+06) | 2.74E+06 (2.15E+06-3.32E+06) | 4.01E+06 (1.58E+06-6.45E+06) |
| Uninfected [n = 2] | 1.43E+05 (0-4.28E+05) | 3.25E+04 (0-1.28E+05) | 1.78E+05 (0-5.27E+05) | 3.20E+05 (0-2.99E+06) | 1.23E+05 (0-9.17E+05) |

[a]95% confidence intervals are in parentheses.
[b]n is number of mice per day per group.

RNA Extraction

For the RNA extraction procedure (see Reference 20), the right lobed lungs were lyophilized for 48 hours. The lyophilized lungs were put in 2-mL tubes with a ceramic spheres sold under the name Lysing Matrix D, sold by MP Biomedicals (Santa Ana, Calif.) and mixed with one mL of a reagent for RNA purification sold under the name TriSure, sold by Bioline USA, Inc. (Taunton, Mass.). Samples were bead beat for two minutes then allowed to incubate for an additional five minutes. 200 microliters (μL) of chloroform was added, mixed well, and incubated for two minutes at room temperature, i.e., 21° C.+/−3° C. Samples were centrifuged at maximum speed for 15 minutes at 4° C. The upper layers were collected and mixed with an equal volume of 80% ethyl alcohol (EtOH), and entire volume pipetted immediately to silica-membrane spin columns sold under the name RNeasy spin columns, sold by Qiagen, Inc. (Valencia, Calif.). The columns were centrifuged one minute, the flow-through discarded and washed twice with kit supplied RPE buffer, i.e., supplied with the RNeasy kit, and columns were completely dried after the last wash. The spin columns were then transferred to new RNase free 1.5 mL tubes, 200 μL of RNase free water was added to each spin column, and incubated for one minute. After the one minute incubation, the tubes containing the spin columns were centrifuged to obtain nucleic acid.

Samples were analyzed with a spectrophotometer sold under the name NanoDrop ND-1000, sold by Thermo Fisher Scientific, Inc. (Waltham, Mass.) and with a cartridge-based molecular assay system sold under the name 2100 Bioanalyzer, sold by Agilent Technologies, Inc. (Santa Clara, Calif.).

Real-Time RT-PCR

Real-time PCR (RT-PCR) was used to detect *Coccidioides* gapdh mRNA extracted from the right lobed lungs of each mouse to determine a relative fungal burden. The right lobed lungs harvested from each mouse underwent real-time RT-PCR analysis to assess transcript level of pro-inflammatory and anti-inflammatory cytokines.

The extracted RNA was treated with a DNase enzyme sold under the name Ambion® Turbo DNA-Free™ kit, sold by Life Technologies Corporation (Carlsbad, Calif.) to remove genomic DNA. The RNA concentration was checked to determine quantity using a spectrophotometer sold under the name NanoDrop ND-1000. The cDNA was produced using a kit for cDNA synthesis sold under the name QuantiTect Reverse Transcription Kit produced by Qiagen (Valencia, Calif.). The real-time RT-PCR was completed using a SensiFAST SYBR® Hi-ROX Mix sold by Bioline USA, Inc. (Taunton, Mass.) on a real-time quantitative PCR system sold under the name ABI7900 sold by Applied Biosystems (Waltham, Mass.). Conditions for real-time RT-PCR were one minute of polymerase activation at 95° C. followed by 40 cycles of 5 seconds at 95° C., 10 seconds at 60° C., and 20 seconds at 72° C.

Figure 1B:
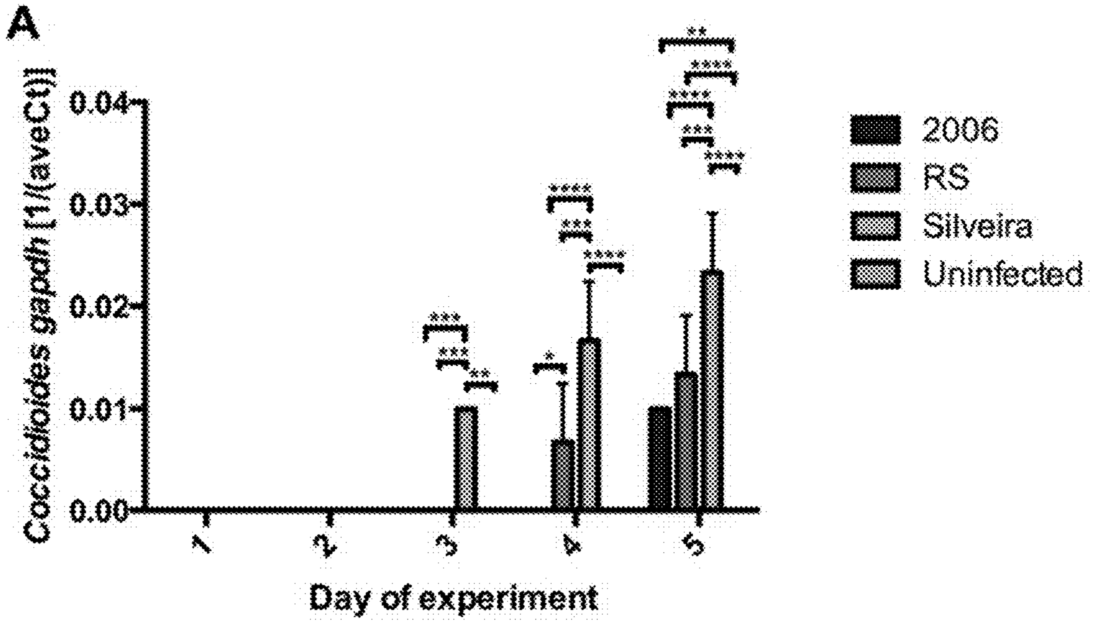

FIG. 1B shows RT-PCR analysis of *Coccidioides* gapdh mRNA transcripts in right lobed lungs of BALB/c mice above signal background. *C. posadasii* isolate Silveira gapdh mRNA transcripts were detected on day three of infection and beyond, whereas *C. immitis* hybrid isolate RS gapdh mRNA transcripts were not detected until day four of infection (see FIG. 1B). *C. immitis* isolate 2006 gapdh mRNA transcripts were not detected until day five of infection. No *Coccidioides* gapdh mRNA transcripts were detected in the uninfected mice.

The cytokine targets and primers used in this Example are listed in TABLE 2 and TABLE 3. To determine fungal burden, oligomers designed to amplify the *Coccidioides* glyceraldehyde-3-phosphate dehydrogenase (gapdh) gene were used in a real-time RT-PCR assay (see TABLE 2).

TABLE 2

DNA oligos used in this Example
Custom Oligos [Coccidioides gene targets]

| Oligo Name | Oligo Sequence (5'→3') | SEQ ID NO |
|---|---|---|
| gapdh forward primer | 5'-ACCAACTGTCTTG CTCCTTTG-3' | 1 |
| gapdh reverse primer | 5'-AGTCTTCTGAGTG GCGGTATAG-3' | 2 |

To examine cytokine gene expression, PrimeTime qPCR primer assays sold by Integrated DNA Technologies, Inc. (Coralville, Iowa) of select genes (see TABLE 3) were used for this Example. Fold change was determined using the 2(-Delta Delta C(T)) method (see Reference 21). The mouse gapdh gene was selected as the internal control gene to calculate the relative expression of the tested mouse genes.

TABLE 3

Primer assays used in this Example
qPCR Primers

| Gene Symbol | Assay ID | Exon Location |
|---|---|---|
| gapdh | Mm.PT.39a.1 | 2-3 |
| ifnγ | Mm.PT.58.30096391 | 3-4 |
| ifnγrl | Mm.PT.58.41904276 | 6-7 |
| il-1α | Mm.PT.58.8990846 | 6-7 |
| il-1β | Mm.PT.58.44004828 | 6-7 |
| il-1rl | Mm.PT.58.28723859 | 10-11 |
| il-2 | Mm.PT.58.11478202 | 1-3 |
| il-4 | Mm.PT.58.42411598.g | 3-3 |
| il-10 | Mm.PT.58.13531087 | 3-5 |
| il-13 | Mm.PT.58.11338747 | 1-3 |
| il-17α | Mm.PT.58.6531092 | 2-3 |
| il-17rα | Mm.PT.58.16204293 | 11-13 |
| tnfα | Mm.PT.58.12575861 | 2-4 |

Real-time RT-PCR results indicate a differential cytokine response dependent on which *Coccidioides* isolate was used for infection.

FIGS. 2A-2K show the RT-PCR analysis of cytokine gene mRNA transcripts in the right lobed lungs of BALB/c mice. Error bars indicate standard error from biological triplicates. P-values were calculated using two-way ANOVA followed by Tukey's multiple comparison test. A p-value<0.05 was considered statistically significant and levels of significance are indicated in FIGS. 2A-2K by asterisks. A single asterisk (*) indicates p≤0.05; two asterisks () indicates p≤0.01; three asterisks (*) indicates p≤0.001; and four asterisks (****) indicates p≤0.0001.

A differential cytokine response was detected among the *Coccidioides* isolates used in this Example. FIG. 2B shows that only the Silveira infection group showed a 20-fold increase in pro-inflammatory cytokine interleukin 1 beta (il-1β). FIG. 2I shows a temporal increasing fold-change trend of the pro-inflammatory cytokine tumor necrosis factor alpha (tnfα) varied among the infection groups during the study. There were also trends that all infection groups shared. FIGS. 2K and 2C show that on day one, there was an initial increase of interferon y receptor 1 (ifnyrl) and interleukin 1 receptor, type I (il-1rl) for all infection groups that significantly decreased on day four and five.

Figure 2A:
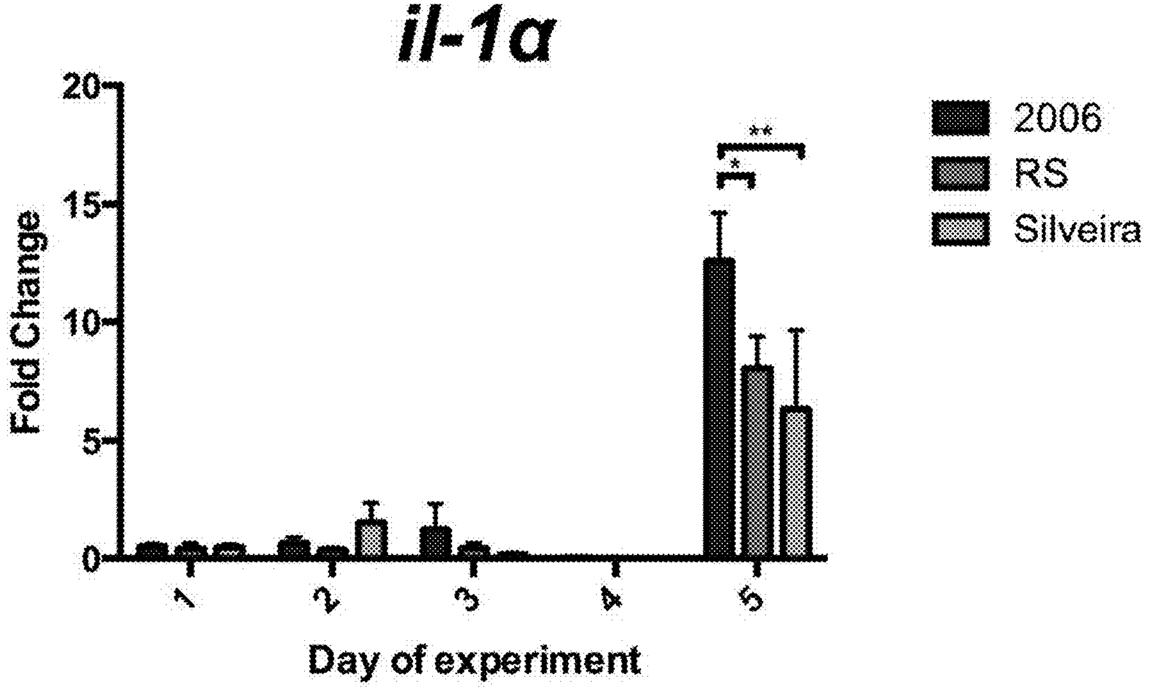
FIGS. 2A-2K illustrate real-time RT-PCR analysis of cytokine gene mRNA transcripts in the right lobed lungs of BALB/c mice.
Figure 2B:
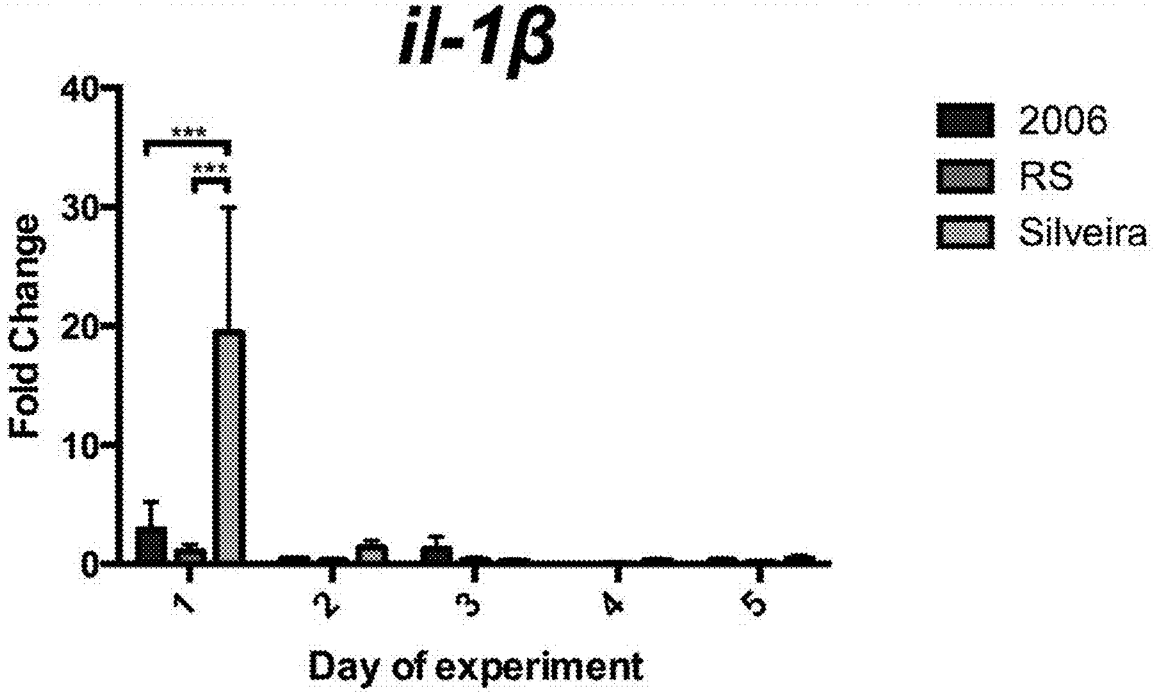
Figure 2C:
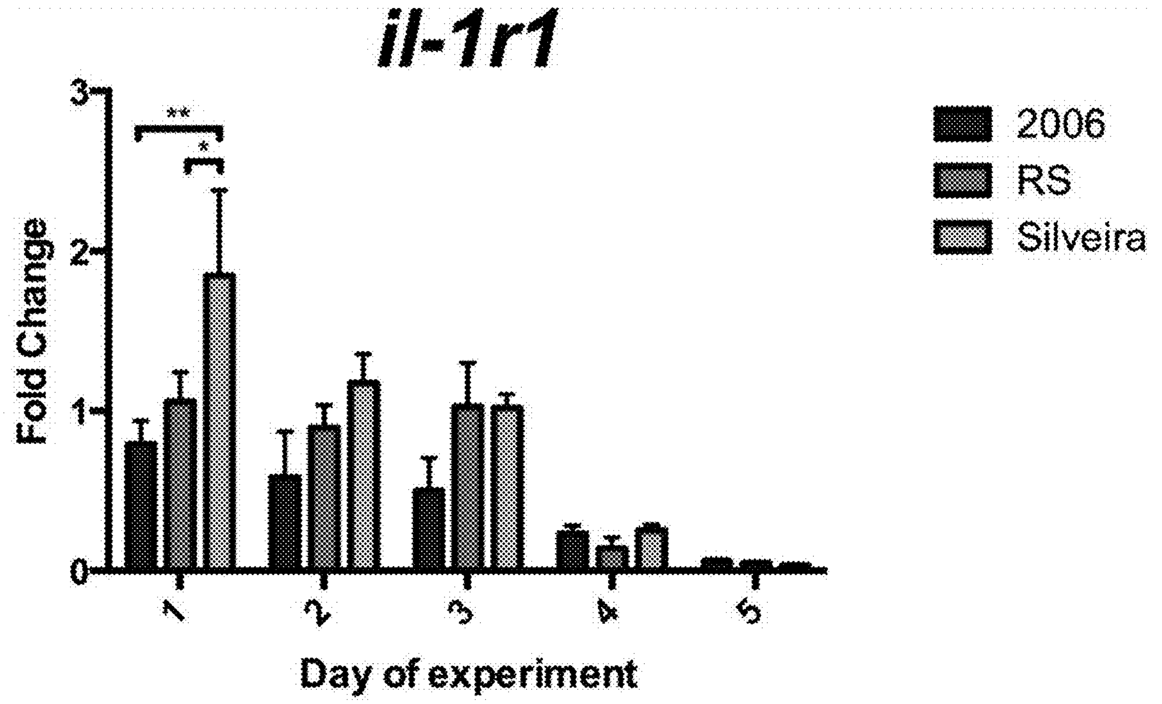
Figure 2D:
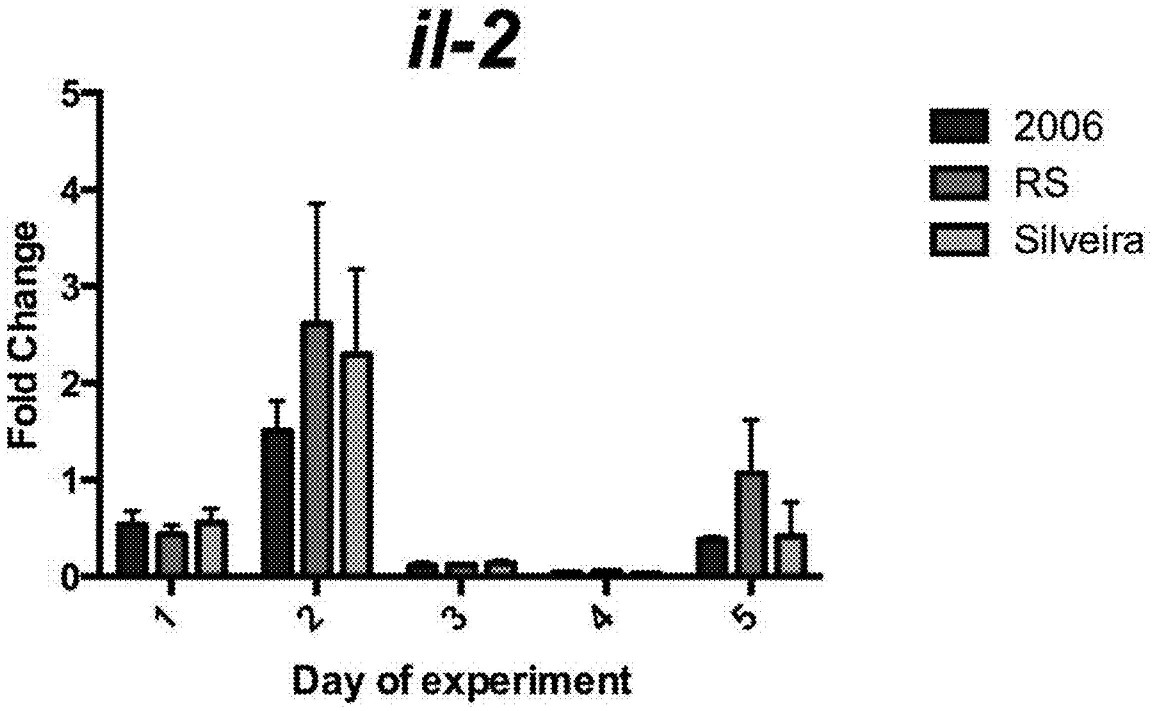
Figure 2E:
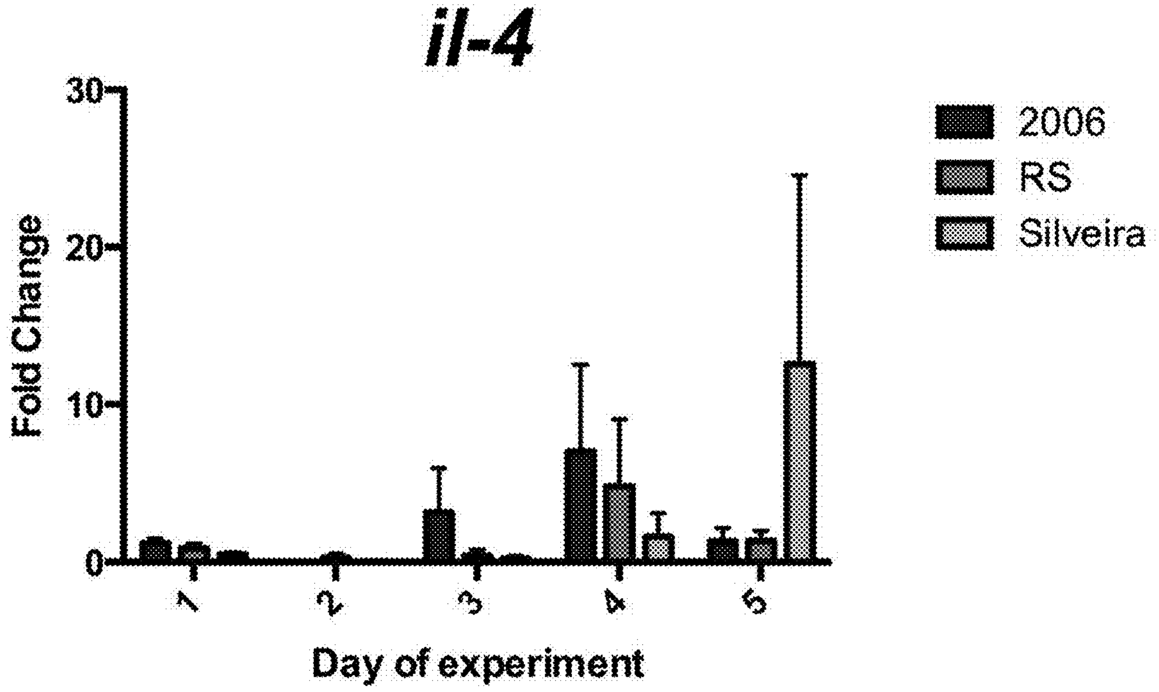
Figure 2F:
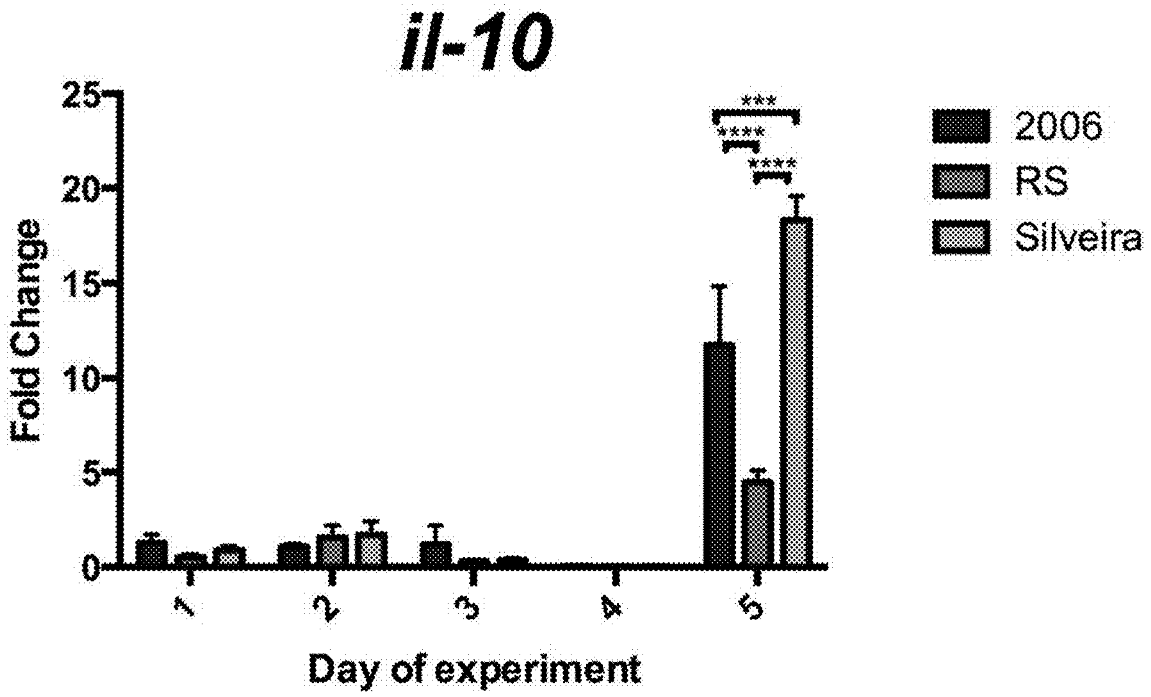
Figure 2G:
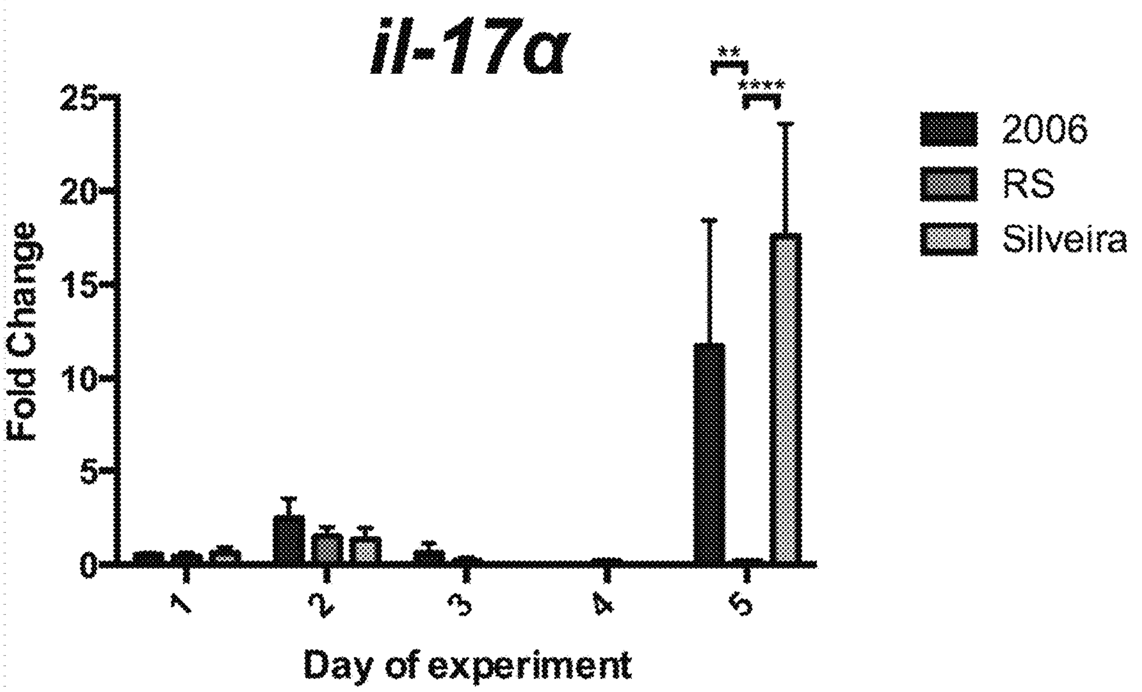
Figure 2H:
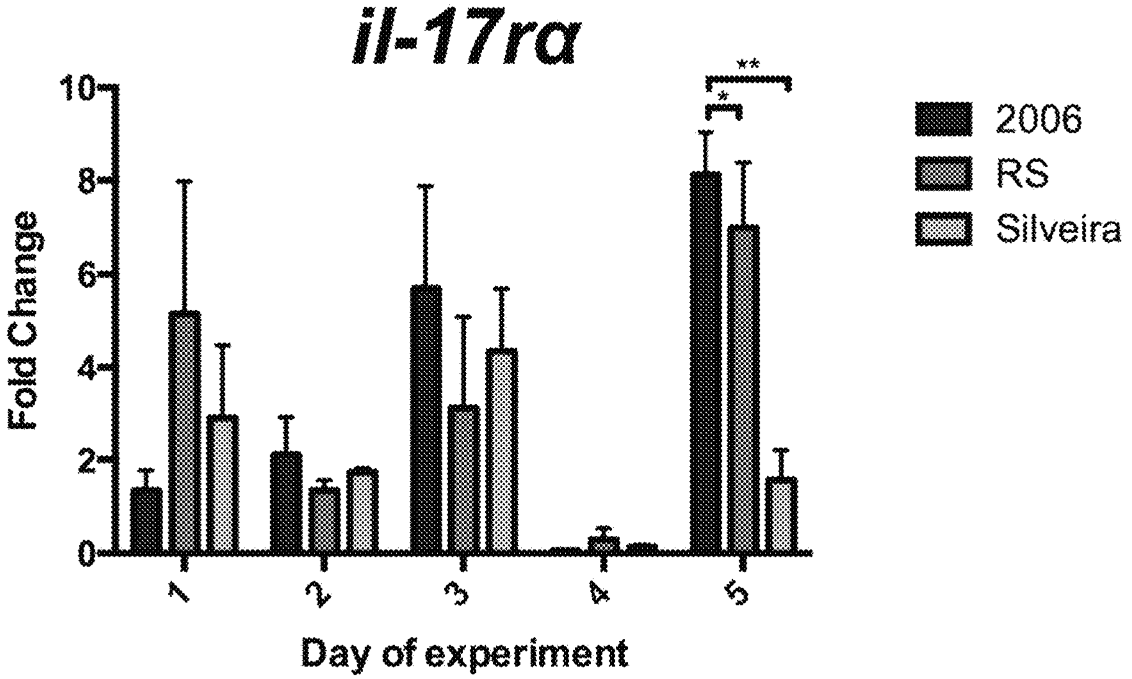
Figure 2I:
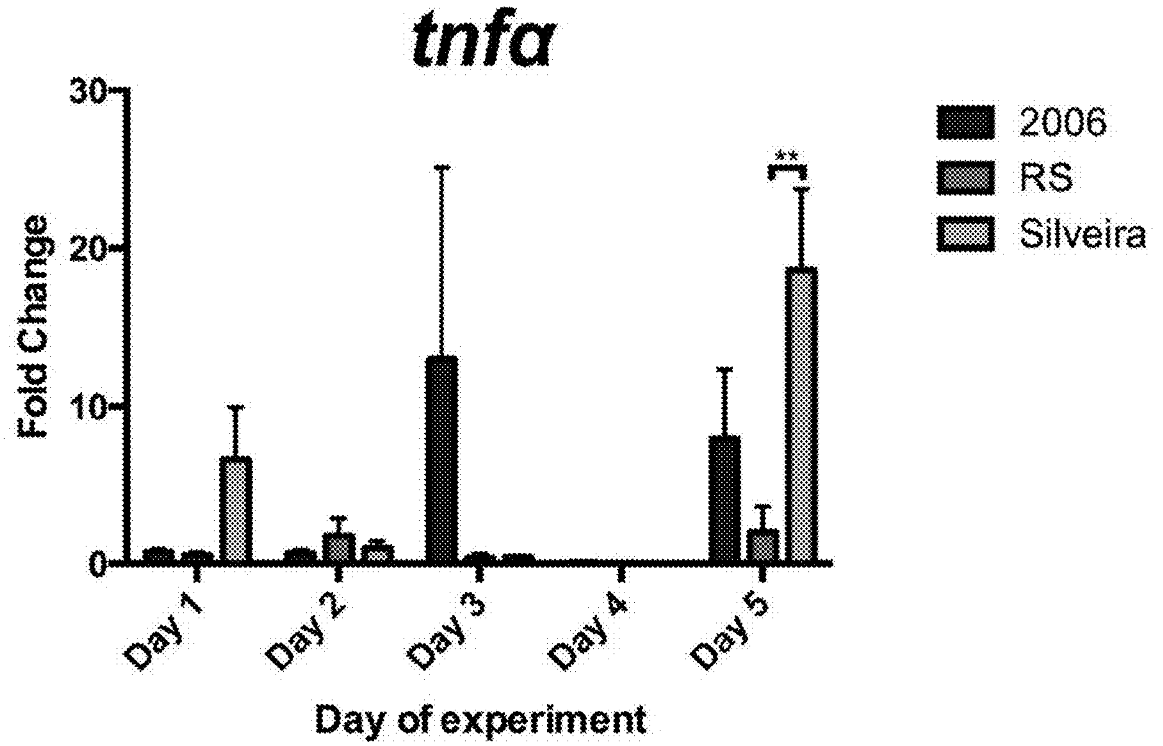
Figure 2J:
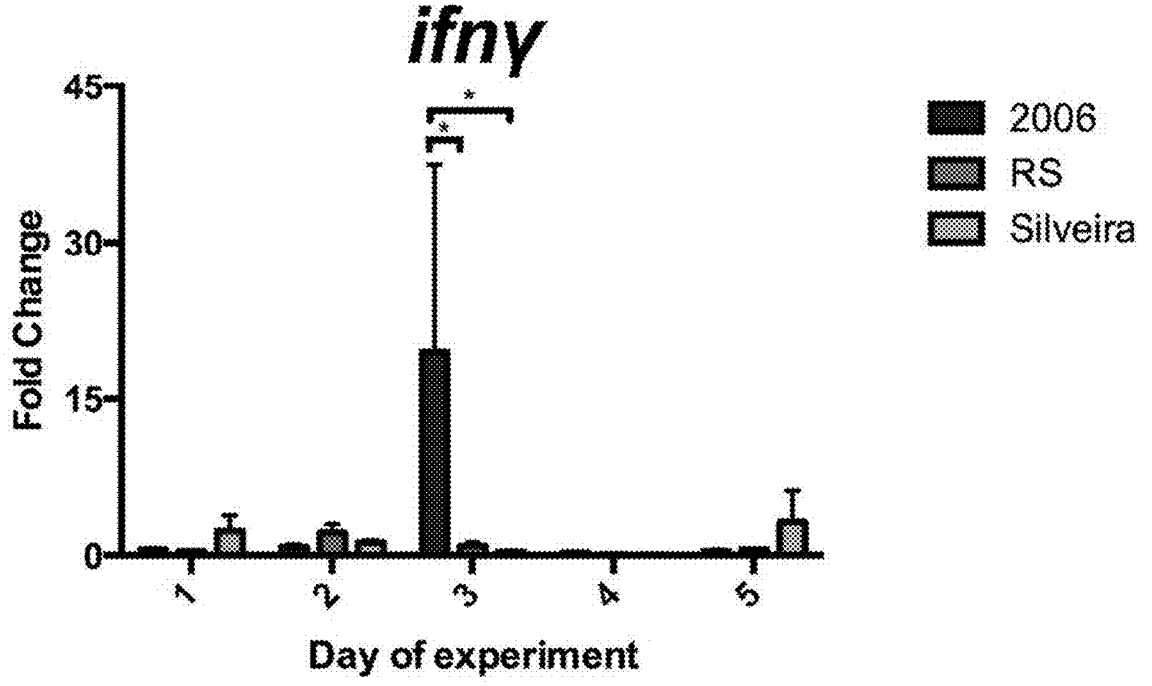
Figure 2K:
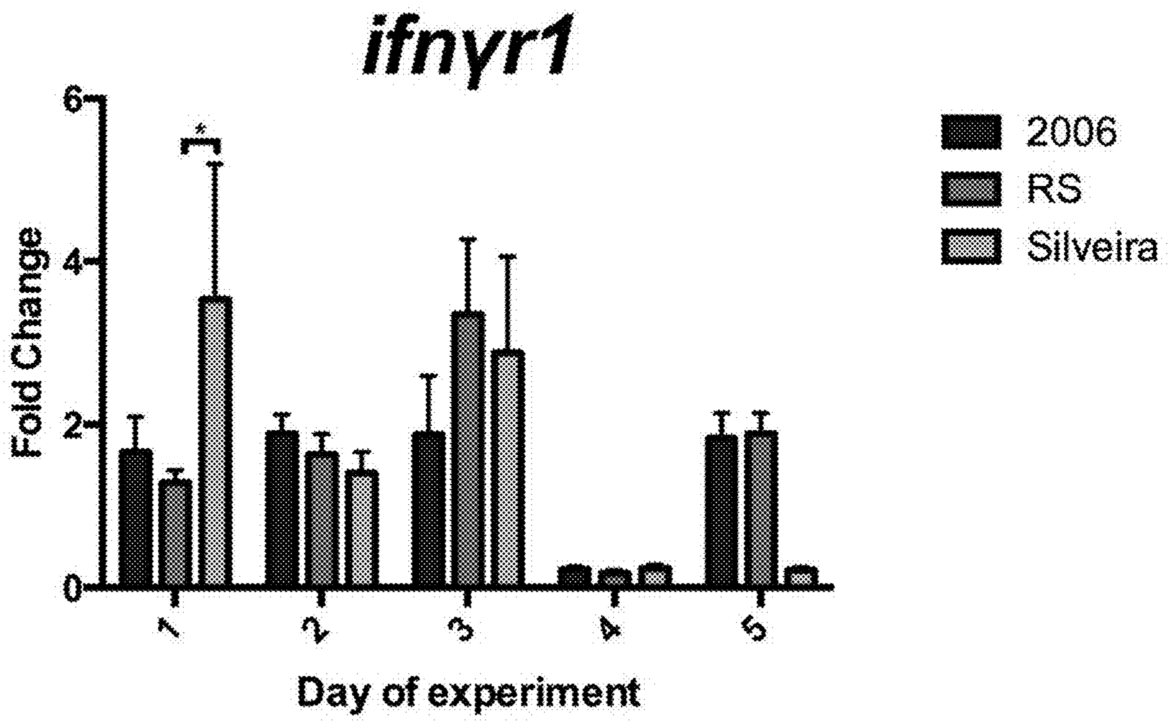

As shown in FIGS. 2F and 2A, there were transcriptional increases for many of the cytokines including anti-inflammatory cytokine interleukin 10 (il-10) and pro-inflammatory cytokine interleukin 1 alpha (il-1α) analyzed on day five of infection for all infection groups. In FIG. 2G, similar increases were seen in the expression of pro-inflammatory cytokine interleukin 17 alpha (il-17α) on day five for the mice infected with 2006 or Silveira. As shown in FIG. 2H, no statistically significant increases were noticed for interleukin 17 receptor alpha (il-17rα) before day five of infection. In FIGS. 2E and 2F, non-statistically significant increases in fold-changes were observed for other transcripts examined including interleukin 2 (il-2) and interleukin 4 (il-4).

Some cytokines including IFNγ can be protective against *Coccidioides* infection in mice, whereas other cytokines including IL4 and IL10 are not protective against infection (see References 6, 7). Other cytokines such as TNFα, IL-1α, and IL-17α have been shown to be protective in murine models of other mycoses (see References 12-14).

In the present Example, the differential cytokine responses involving both probable protective and non-protective cytokines observed in this Example may associate with the inability of BALB/c mice to respond to *Coccidioides* infections.

Multiplex Bead Array Assay

Cytokine concentrations were measured using a multiplex bead array and normalized to the amount of total protein quantified in each sample. Twenty cytokines were quantified.

The concentrations of the twenty cytokines for the BALFs were examined using a suspension bead-based multiplex assay sold under the name Cytokine Mouse Magnetic 20-Plex Panel, sold by Life Technologies (Carlsbad, Calif.) on a multiplex analyzer sold under the name Luminex LX200 system with Luminex xPONENT 3.0 software sold by Luminex Corporation (Austin, Tex.). The Cytokine Mouse Magnetic 20-Plex Panel included cytokines: GM-CSF, IFN-γ, IL-1α, IL-1β, IL-2, IL-4, IL-5, IL-6, IL-10, IL12 (p40/p70), IL-13, IL-17, and TNFα; chemokines: IP10, KC, MCP-1, MIG, and MIP-1α; and growth factors: FGF-Basic, and VEGF.

A bicinchoninic acid (BCA)-based assay for the colorimetric detection and quantification of total protein, sold under the name BCA Protein Assay sold by Thermo Scientific Pierce (Life Technologies, Carlsbad, Calif.) was used to quantify protein concentrations. Cytokine concentrations were normalized to the amount of total protein quantified in each sample. Few were detected above the assay's lower limit threshold as only IFNγ and IL-2 were detected in the BALFs using this method. Overall, an abundant cytokine response was not detected.

Figure 3A:
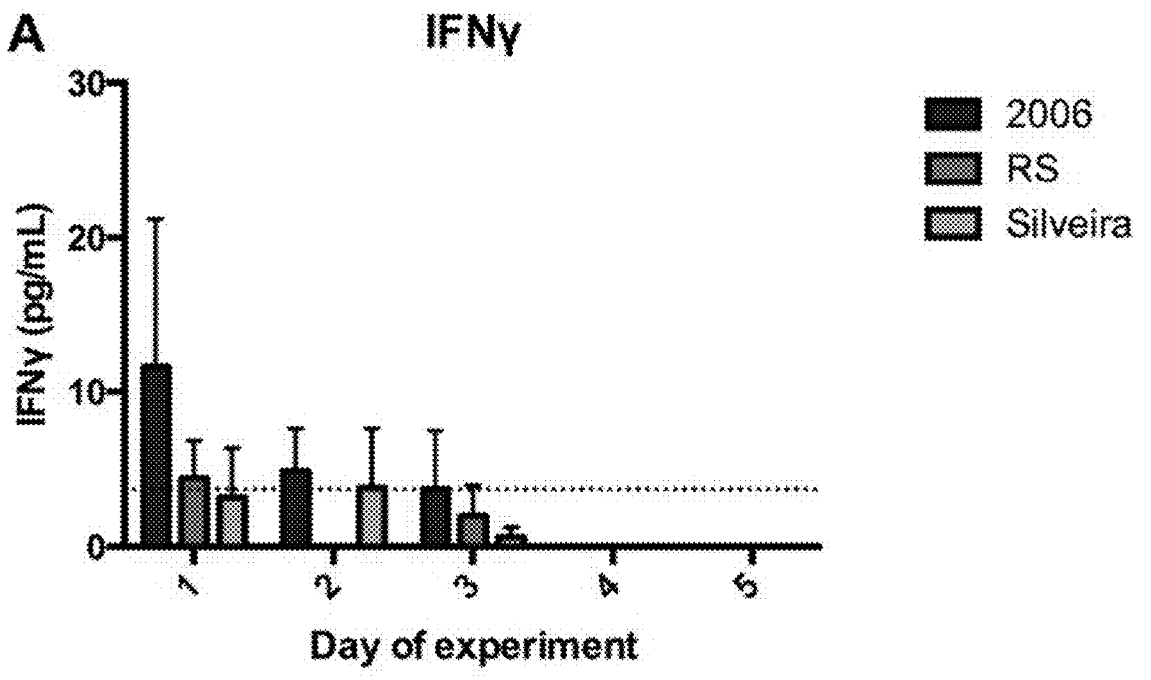
FIGS. 3A-3B illustrate concentration of cytokines.
Figure 3B:
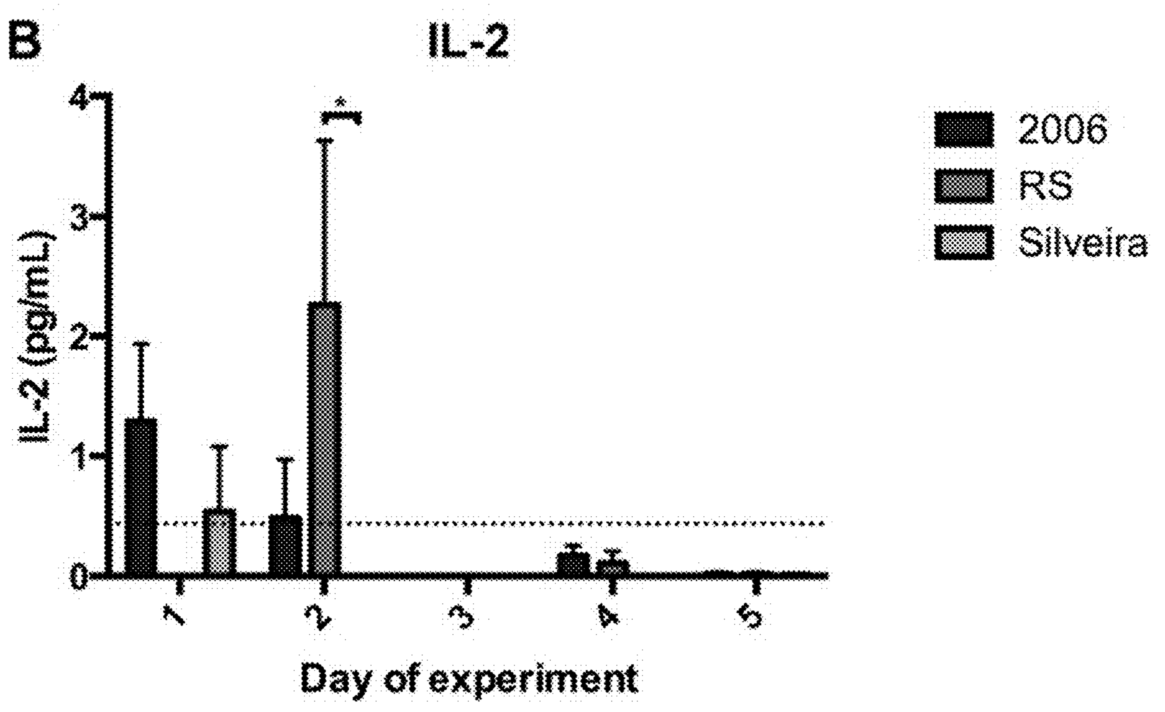

In FIGS. 3A and 3B, the average values of protein concentration in pictograms per milliliter (pg/mL) for IFNγ and IL-2 in uninfected control animals are represented by dashed lines. Error bars indicate standard error from biological triplicates. P-values were calculated using two-way ANOVA followed by Tukey's multiple comparison test. A p-value<0.05 was considered statistically significant and levels of significance are indicated in FIGS. 3A and 3B by asterisks. A single asterisk (*) indicates p≤0.05.

FIG. 3A shows concentration of cytokine IFNγ. During the five days of infection, day one appeared to be the only day in which IFNγ was at higher, but non-statistically significant, concentration in the 2006 group when compared to the uninfected group. FIG. 3B shows concentration of cytokine IL-2. On day one of infection, a non-statistically significant increase of IL-2 was present in the BALFs of infection groups 2006 and Silveira. Abundant cytokine proteins were not detected in the BALFs using the multiplex bead array assay. Because few cytokine proteins were detected, proteomic analysis on the samples collected on day five of infection allowed for determination of other proteins present.

Proteomic Analysis

Proteomics analysis was employed on remaining BALFs. Proteomic analysis was performed on the BALFs collected on day five of the experiment from the nine infected mice (three mice per infection group) and the two mice in the uninfected group. Equal amounts of protein (20 μg each) were reduced and denatured by boiling for 10 min in loading buffer sold by Bio-Rad Laboratories, Inc. (Hercules, Calif.) containing 5% β-mercaptoethanol. Each sample was then separated by gel electrophoresis on a 4-20% sodium dodecyl sulfate polyacrylamide gel electrophoresis (SDS-PAGE gel), sold by Bio-Rad Laboratories, Inc. (Hercules, Calif.) for 45 minutes at 120 V and stained using a colorimetric protein assay sold under the name Coomassie Plus, sold by Bio-Rad Laboratories, Inc. (Hercules, Calif.). Gel lanes were fully excised into individual bands, destained, washed, dried and further processed using a previously published method (see Reference 22). Briefly, each lane fraction was reduced and alkylated using cyclic rehydration/dehydration of the acrylamide gel slabs. Samples were then digested using a protease sold under the name Trypsin Gold, sold by Promega Corporation (Madison, Wis.), at 20 ng/mL overnight at 37° C. Peptides were extracted, concentrated to dryness under vacuum and frozen at −20° C. prior to mass spectrometry analysis.

Analyses were conducted on a system for analyzing compounds and introducing separated samples in to a mass spectrometer, the system sold under the name nanoAcquity-UPLC system sold by Waters Corporation (Milford, Mass.), coupled to a mass spectrometer sold under the name Thermo LTQ Orbitrap Velos, sold by Thermo Scientific (Waltham, Mass.). Each sample fraction was reconstituted in 0.1% formic acid for analysis by using online liquid chromatography coupled to mass-spectrometry. Each fraction was reconstituted in 0.1% formic acid and loaded onto a 100-micrometer (μm) diameter column packed to 100 millimeter (mm) with 3 μm Reprosil Pur C18 AQ resin, eluted at 500 nanoliter per minute (nL/minute). Solvent A and B were 0.1% formic acid in water and acetonitrile, respectively. The gradient was 3% B to 40% B in 17 minutes followed by 40% B to 90% B in 0.5 minutes, then 90% B for 2 minutes and re-equilibration for 10.5 minutes. The mass spectrometer operated in positive ion mode using a spray voltage of 1.8 kV, and a capillary temperature of 200° C. Data were acquired in top-15, data-dependent acquisition mode using a collision voltage of 30 V.

Raw mass spectrometry data were searched against a concatenated database from UniprotKB/Swissprot for *Mus musculus*, and UniprotKB/Swissprot+Trembl for *C. posadasii* isolate Silveira and *C. immitis* isolate RS using Mascot (Matrix Science, London, UK; version 1.4.1.14) and X! Tandem (The GPM, v2010.12.01.1). Tandem mass spectra were extracted, charge state was deconvoluted and deisotoped by Proteome Discoverer 1.4.1.14 (Thermo Fisher Scientific, Waltham, Mass.). Oxidation (Met), carbamidomethylation (Cys), and pyroGlu formation (N-terminal Gln or Glu) were specified as variable modifications. A peptide mass tolerance of ±10 ppm, a fragment mass tolerance of ±0.8 Da, and a maximum of two trypsin missed cleavages were allowed. Peptide identifications were accepted at greater than or equal to (≥) 98.0% as specified by the Peptide Prophet algorithm (see Reference 23) and corrected using Scaffold m correction sold by Proteome Software Inc. (Portland, Oreg.). Varying amounts of total protein in BALFs were quantified.

Figure 4:
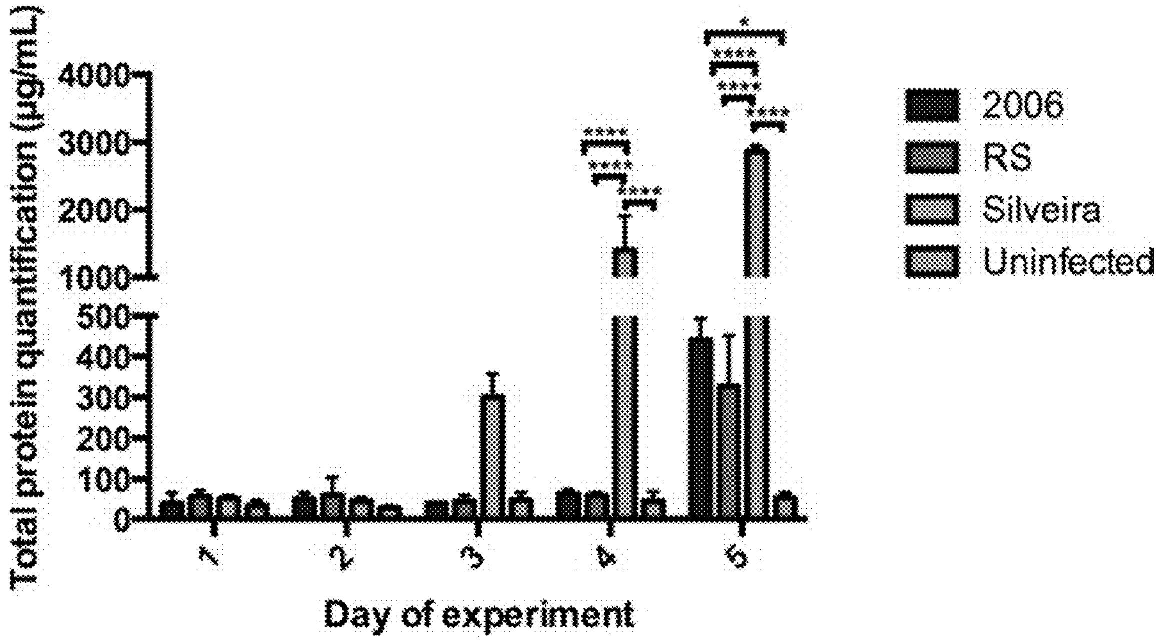
FIG. 4 illustrates the concentration of total proteins present in BALFs.

FIG. 4 shows the concentration micrograms per milliliter (μg/mL) of total proteins present in BALFs. Overall total protein concentrations remained below 100 μg/mL within all of the mouse groups until day three of infection. Error bars indicate standard error from biological replicates (n=3 for each infection group, n=2 for the uninfected group). P-values were calculated using two-way ANOVA followed by Tukey's multiple comparison test.

On day three of infection the Silveira infected mice reached a mean total protein concentration of 300 μg/mL while other mouse groups remained below 100 μg/mL. A marked increase in the mean total protein concentration within the BALFs of the Silveira infection group on day four was statistically significant when compared to the 2006 infection group (p≤0.0001), RS infection group (p≤0.0001), and uninfected mouse group (p≤0.0001). On day five all infection groups had increased levels of total protein present in BALFs compared to the uninfected mouse group. Silveira appeared to be the most virulent isolate studied in this Example. Increasing levels of the total protein during the course of this study was likely due in part to lung damage caused by infection. Differences in the proteomic profile suggests that lung damage was not the only cause of increased protein concentration. Non-interleukin proteins involved in inflammation, immune signaling, and host defense response proteins were in varying abundance for all infection groups compared with uninfected mice. Similar to the cytokine response to infection, the proteome of the BALFs varied depending on which isolate was used for infection. Some identified proteins and specific host response pathways may be useful host biomarkers for pulmonary coccidioidomycosis. As the highest protein concentrations were observed at day five, downstream proteomic analysis was performed on these samples.

Figure 5:
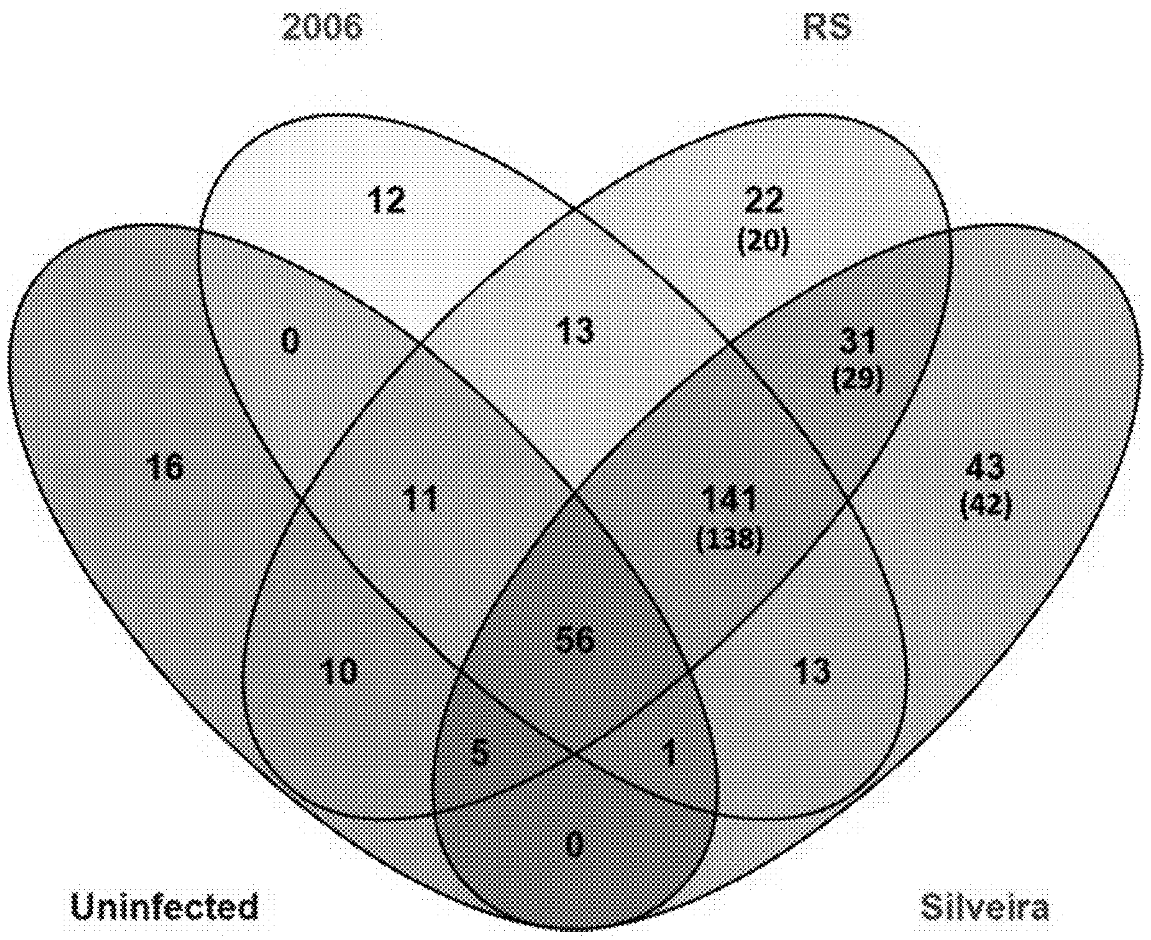
FIG. 5 illustrates a Venn Diagram comparing and contrasting the number of unique proteins identified in the BALFs collected from the day five groups using mass spectrometry analysis.

FIG. 5 shows a Venn Diagram comparing and contrasting the number of unique proteins identified in the BALFs collected from the day five groups using mass spectrometry analysis. A total of 374 total unique proteins were identified from the proteome of all BALFs collected on day five of this experiment. The total of 374 unique proteins composed of 366 unique mouse proteins, and eight unique *Coccidioides* proteins were identified among the infected mice. In parentheses in FIG. 5 is the number of mouse proteins that were only identified in a particular group. Of the proteins that identified, 33 mouse proteins displayed statistically significant differences between the four mouse groups examined in this study.

Six mouse proteins shown in TABLE 4 were significantly differentially abundant in uninfected mice when compared to all of the mouse infection groups.

TABLE 4

Mouse proteins significantly differentially expressed in uninfected mice compared to other groups on day five of the experiment

| Protein Name | Gene ID | Abundance |
|---|---|---|
| Alpha-2-macroglobulin | A2M_MOUSE | Less |
| Aminopeptidase N | AMPN_MOUSE | More |
| Annexin A5 | ANXA5_MOUSE | More |
| Complement C3 | CO3_MOUSE | Less |
| Hemopexin | HEMO_MOUSE | Less |
| Proteasome subunit beta type-6 | PSB6_MOUSE | Less |

Two of the six mouse proteins in TABLE 4, annexin A5 and aminopeptidase N, were increased in all uninfected as compared to infected mice. Aminopeptidase N extracellular signaling helps to reduce inflammation, and annexin a5 is a known inhibitor of protein kinase C, thus inhibiting apoptosis and degranulation in healthy mice (see References 26, 27). This suggests activation of cytotoxic activity from mast cells, granulocytes, and activation of inflammation and apoptosis in all infected mice. Four of the proteins, α-2-macroglobulin, complement C3, hemopexin, and proteasome subunit are lower in uninfected and these are associated with general lung damage and inflammation common in all the infected mice (see References 28-31).

As shown in TABLE 5, twelve mouse proteins were significantly differentially expressed for mice infected with RS when compared to the other mouse groups.

TABLE 5

Mouse proteins significantly differentially expressed in RS infected mice compared to other groups on day five of the experiment

| Protein Name | Gene ID | Abundance |
|---|---|---|
| Afamin | AFAM_MOUSE | More |
| Apolipoprotein A-I | APOA1_MOUSE | More |
| Chitinase-3-like protein 1 | CH3L1_MOUSE | More |
| Cluster of Chitinase-like protein 3 | CHIL3_MOUSE | More |
| Cluster of Hemoglobin subunit beta-1 | HBB1_MOUSE [2] | More |
| Ferritin light chain 1 | FRIL1_MOUSE | More |
| Fibronectin | FINC_MOUSE | Less |
| Inter alpha-trypsin inhibitor, heavy chain 4 | ITIH4_MOUSE | Less |
| Leukemia inhibitory factor receptor | LIFR_MOUSE | More |
| Polymeric immunoglobulin receptor | PIGR_MOUSE | More |
| Serotransferrin | TRFE_MOUSE | More |
| Triosephosphate isomerase | TPIS_MOUSE | More |

10 of the 12 mouse proteins in TABLE 5 were more abundant, including chitinase and iron/heme associated genes. For the proteins that were lower in abundance, fibronectin and inter α-trypsin inhibitor are both biomarkers associated with COPD and inflammatory processes when found in abundance, suggesting that RS does not induce inflammation via this mechanism (see References 31, 32).

In TABLE 6, ten mouse proteins were significantly differentially expressed proteins and were found in mice infected with Silveira compared to the other groups.

TABLE 6

Mouse proteins significantly differentially expressed in Silveira infected mice compared to other groups on day five of the experiment

| Protein Name | Gene ID | Abundance |
|---|---|---|
| Carbonic anhydrase 2 | CAH2_MOUSE | Less |
| Carbonyl reductase [NADPH] 2 | CBR2_MOUSE | Less |
| Ceruloplasmin | CERU_MOUSE | More |
| Complement C5 | CO5_MOUSE | Less |
| Fibrinogen beta chain | FIBB_MOUSE | More |
| Gelsolin | GELS_MOUSE | More |
| Histone H4 | H4_MOUSE | More |
| Inter alpha-trypsin inhibitor, heavy chain 4 | ITIH4_MOUSE | More |
| Lactotransferrin | TRFL_MOUSE | Less |
| Thioredoxin | THIO_MOUSE | More |

Of the four mouse proteins in TABLE 6 that are less abundant, carbonic anhydrase 2 and carbonyl reductase (NADPH) 2 suggest a non-protective response to oxidative stress, whereas complement C5 and lactotransferrin suggest a lack of protective inflammatory response (see References 29, 33-35). For proteins that were more highly expressed, all are associated with damage response, supporting the observation that Silveira causes significant damage to the lung. Interestingly, no unique proteins were differentially abundant for mice infected with isolate 2006.

In addition to finding differential host protein expression profiles, at least three *Coccidioides* proteins were also identified that have been shown to be associated with the *Coccidioides* parasitic life cycle, validating that the present method of proteomic analysis was able to detect expected proteins. Some of the *Coccidioides* proteins that were identified are uncharacterized proteins, including a protein (CIMG_09001/CPSG_01366) that was identified in all infection groups. Proteins associated with infections caused by both *Coccidioides* species may be necessary for the initiation of the parasitic life cycle, and therefore may be targets for diagnostics and/or therapeutics.

Many *Coccidioides* isolates tested to date cause fatal disease within eight to twelve days with as few as 50 arthroconidia administered intranasally in immunocompetent BALB/c mice (see References 17, 48). In the present example, 100,000 arthroconidia were administered intranasally to each group and had potential to overwhelm the host innate immune response. The data suggest that host innate immune response was not overwhelmed, and is reasonable when considering dosages administered for other fungal pathogens (see References 49-51). As discussed, a differential cytokine response to *Coccidioides* isolates used in the study was observed and the early innate immune response did not seem overly robust. The dose administered to the mice in the present study is biologically relevant, as a host could inhale 100,000 or more arthroconidia during an acute environmental exposure.

The lack of a strong cytokine response to early pulmonary coccidioidomycosis described in this study points to previous studies suggesting host immune system evasion. Circulating *Coccidioides* antigens have been shown to suppress cell-mediated immune response in BALB/c mice (see References 6, 53, 54). More recently, the virulence factors spherule outer wall glycoprotein (SOWgp) and metalloproteinase 1 (Mep1) were identified and shown to evade the host immune response in a C57BL/6 mouse model of coccidioidomycosis (see References 55-59). The more successful pathogens utilize one or several mechanisms to evade and/or counteract a protective immune response from the host (see References 60-62). Because these previously identified protein products were not identified in this Example, *Coccidioides* may utilize additional host immune evasion mechanisms, and these may differ temporally as well as among isolates.

Biological Concept Enrichment Analysis

In order to determine representative biology associated with the four sets of proteins (uninfected, 2006, RS and Silveira), the application ClueGO was used to perform biological concept enrichment analysis. ClueGO visualizes the functional enrichment results by grouping similar ontologies and networks into overlapping clusters based on similar function and gene membership. Biological concept enrichment analysis was performed on the four sets of proteins using the ClueGO v2.1.7 Cytoscape plugin (see Reference 24).

Figure 6:
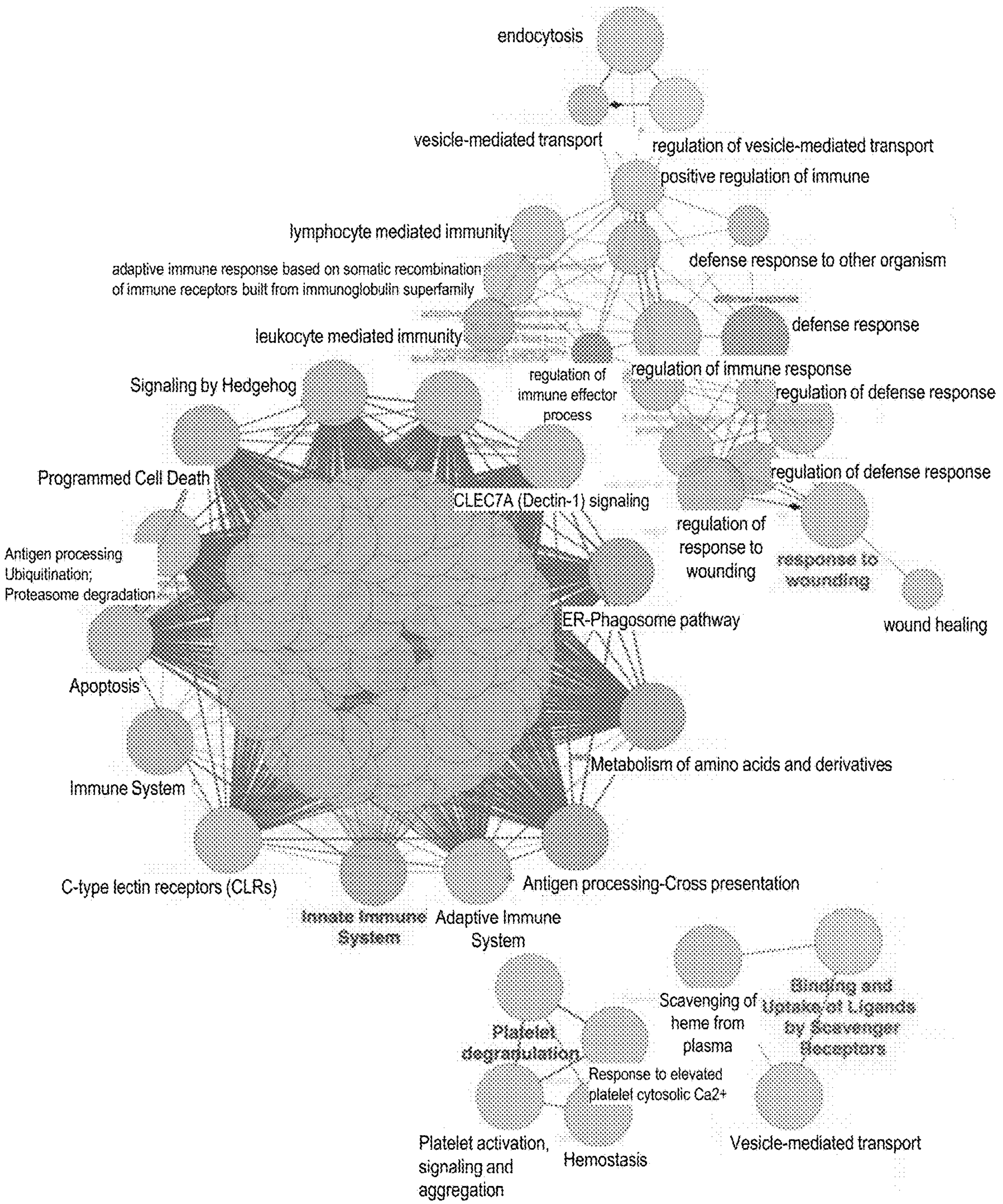
FIG. 6 illustrates an enrichment network diagram of the four sets of proteins identified in the BALFs collected from the day five groups.
Figure 6:
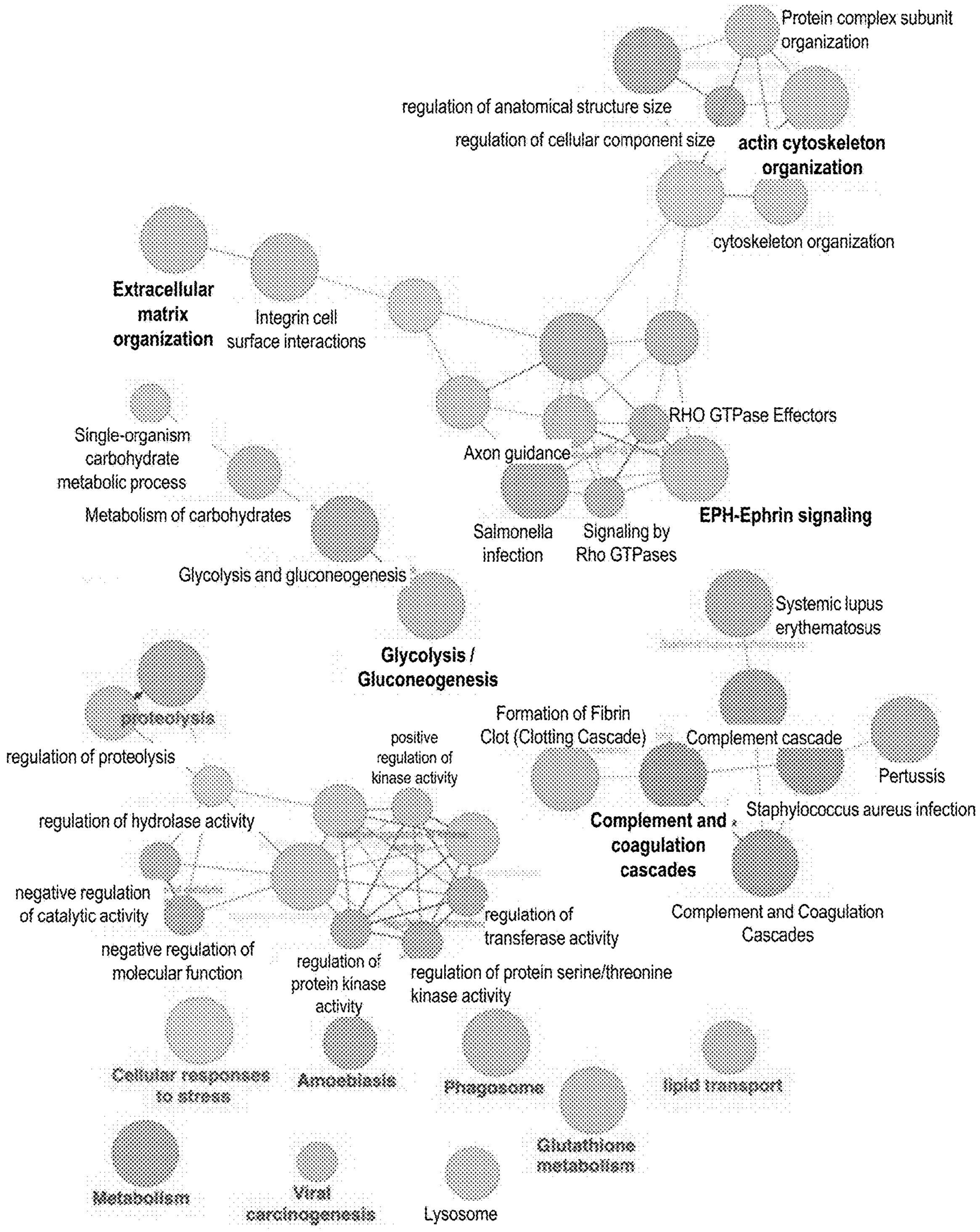
Figure 7A:
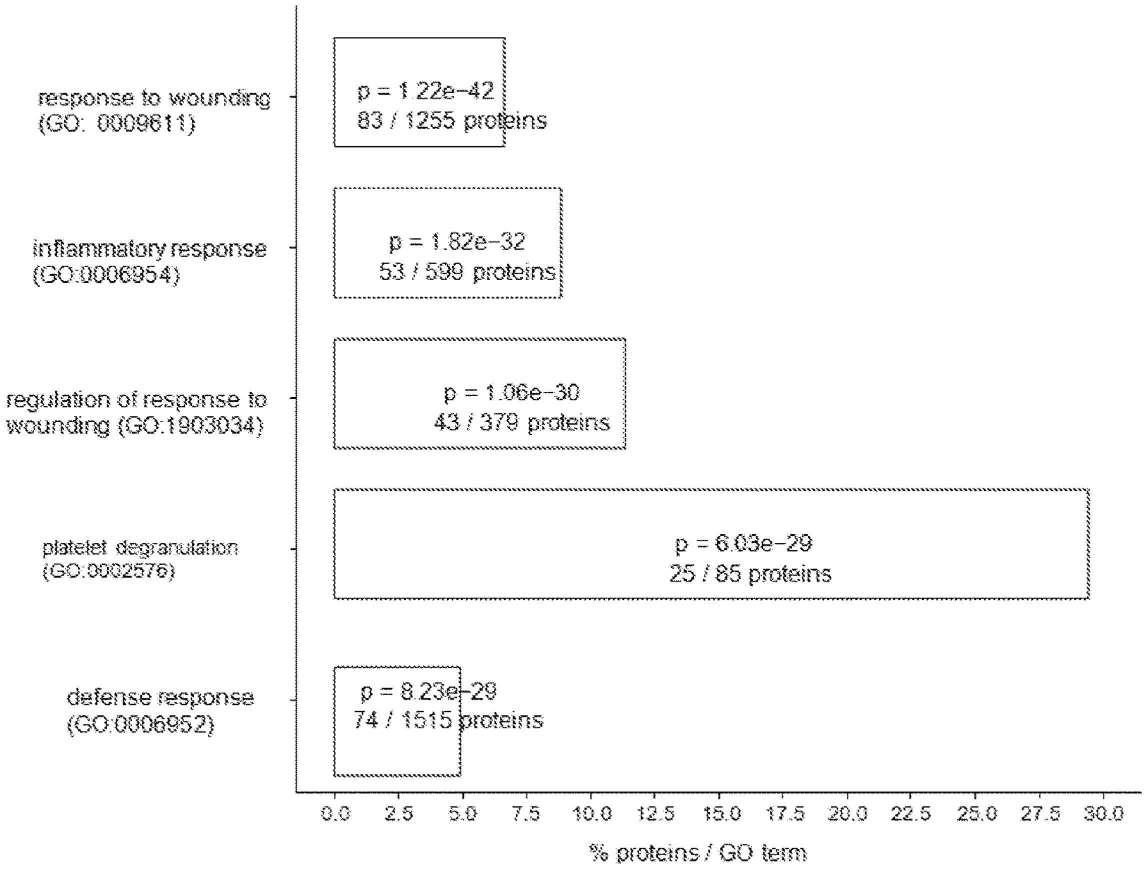
FIGS. 7A-7D illustrate a ToppGene enrichment analysis of mouse proteins identified in BALFs collected from the Silveira infection group on day five of the experiment.
Figure 7B:
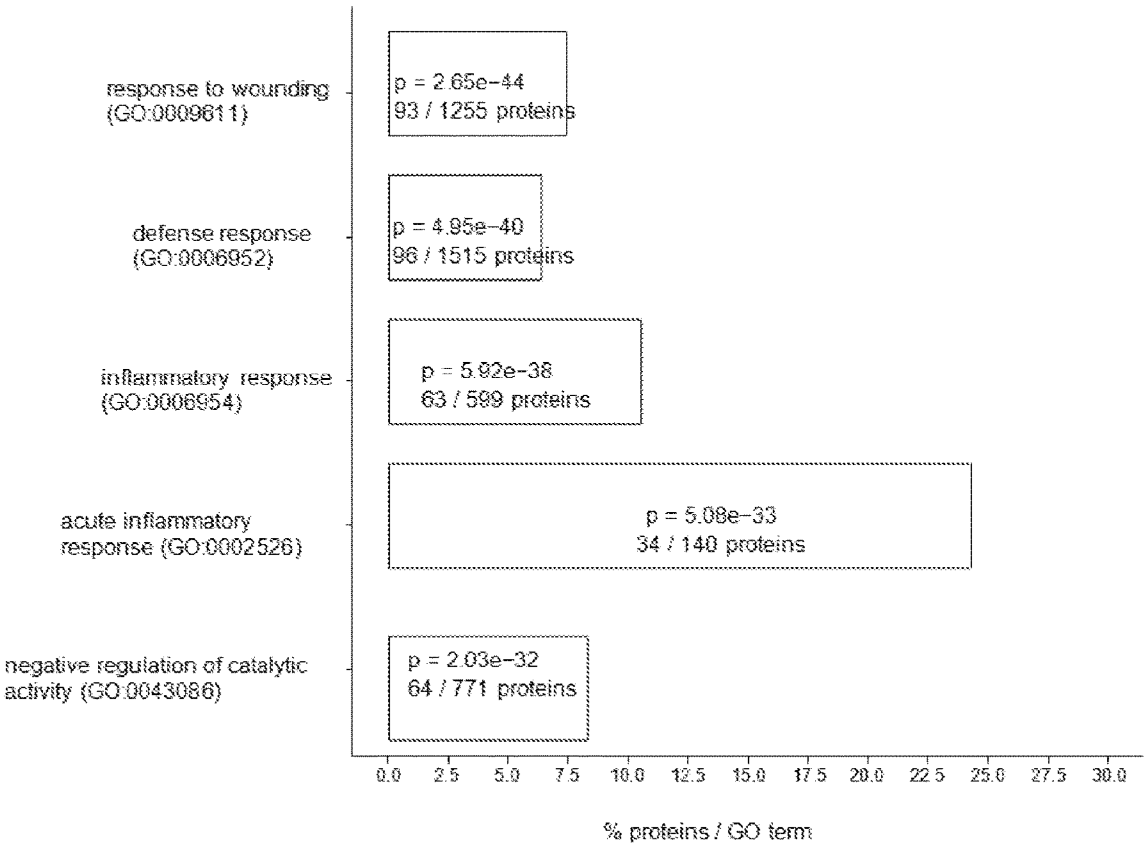
Figure 7C:
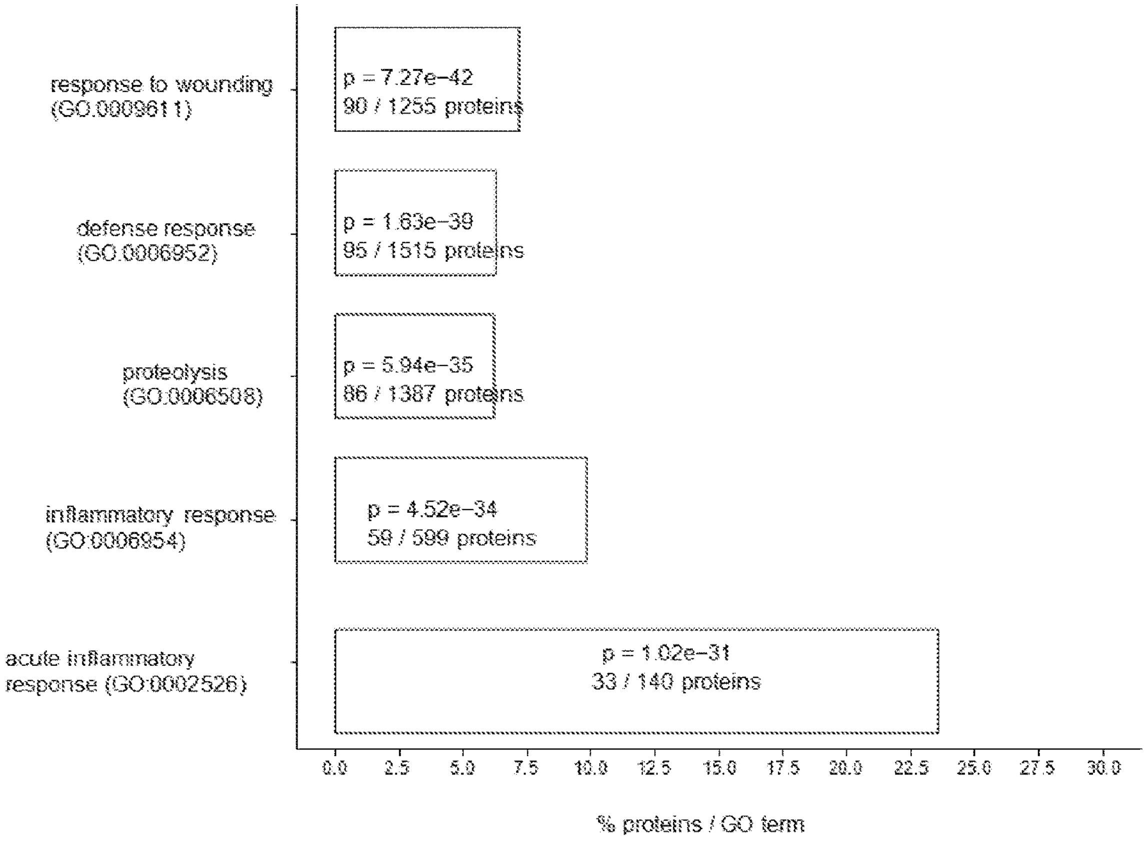
Figure 7D:
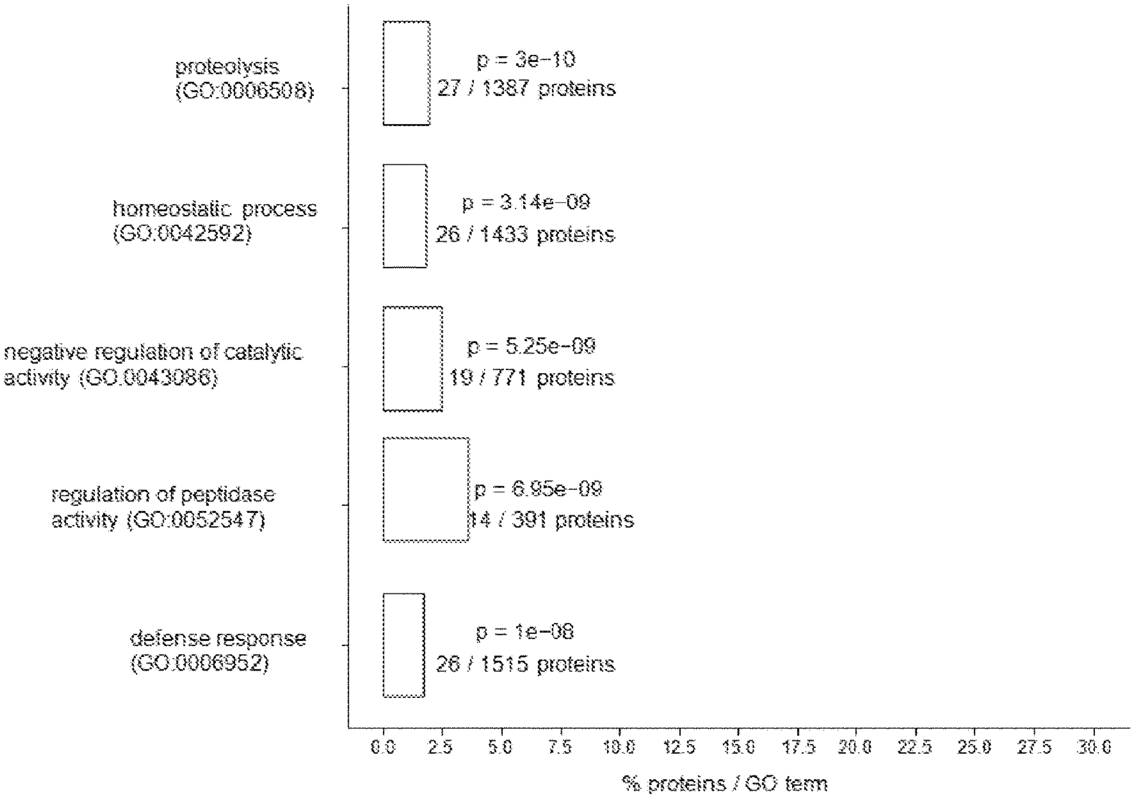

FIG. 6 shows the enrichment network diagram for the four sets of proteins. The four protein sets were analyzed with ClueGO using the GO Gene Ontology (GO) Biological Process, Kyoto encyclopedia of genes and genomes (KEGG), Reactome, and WikiPathways gene set categories. Advanced Term/Pathway selection options were set at Go Tree Interval Minimum level 3 and Max level 8, GO term fusion, and minimum number of genes at five for uninfected and ten for 2006, RS, and Silveira). The kappa score was set at 0.4. A two-sided hypergeometric test was used with Bonferroni step down correction.

The nodes in the diagram represent enriched ontologies or pathways. The red nodes represent ontologies or pathways that show preferential enrichment in the Silveira strain. The blue nodes are those enriched in the RS group of proteins. No category had preferential enrichment for proteins in the 2006 or uninfected protein set. The grey nodes did not have a preferential enrichment in any of the protein sets and represent common terms in all protein sets. Node size corresponds to p-value significance. The edges represent the statistical association between the nodes based on gene membership and location with gene ontology. The bold node labels represent those nodes of most significant term for cluster of nodes.

The significant ontology/pathway nodes for the Silveira infection group protein set (red nodes) were categories such as innate immune system, proteolysis, cellular response to stress, lipid transport, EPH-Ephrin signaling, and actin cytoskeleton organization. The protein set from the RS infection group (blue nodes) had significant node clusters, such as metabolism, phagosome, complement and coagulation cascades, as well as glutathione metabolism, among others. A tight cluster of nodes is centered on signaling pathways with a large component of proteasome-related gene. A cluster of proteasome genes common across all protein sets are driving enrichment in this cluster of pathways.

Gene Functional Analysis

A functional enrichment analysis, using a system by the name of ToppGen, was also performed to confirm the results of the protein clustering analysis. The ToppGene functional analysis suite (see Reference 25) was used to identify enriched terms in each of the four sets of proteins (uninfected, 2006, RS, and Silveira) (FDR correction, p-value<0.05, gene limits 1≤n≤2000).

FIGS. 7A-7D show the ToppGene enrichment analysis of mouse proteins identified in BALFs collected from the Silveira infection group on day five of the experiment. Enriched terms from the biological process ontology were ranked by p-value and the five most significant terms were retained for interpretation of the host response to *Coccidioides* infection in BALFs.

FIGS. 7A-7D show that the host proteins identified align with the increase in *Coccidioides* isolate fungal burden and infection dynamics (2006<<RS<<Silveira) observed in other assays. Total proteins assigned to these terms were notably lower in uninfected mice, possibly as a result of a baseline defense response to challenges at the endothelial interface between alveoli and capillaries. Key terms associated with inflammation were present in all *Coccidioides* isolate groups. Proteins associated with both innate and humoral response were prioritized for RS and Silveira (defense, inflammatory and acute inflammatory response). Proteins secreted in response to wounding were significant in all infection groups confirming the findings of likely lung damage and tissue necrosis. An increase of platelet degranulation associated proteins was detected in the 2006 mouse infection group that was not as apparent in the other infection groups or uninfected control mice. Platelet degranulation is an antimicrobial host response to infection that has been observed for other human pathogens including the fungus *Aspergillus fumigatus* and multiple bacterial species (see References 36 and 37). The high fungal burden of Silveira isolate also likely led to an increase in proteolytic host response.

TABLE 7 shows the identified *Coccidioides* proteins present in BALFs.

TABLE 7

Coccidioides proteins that were detected in the BALFs collected from the infected mice on day five of infection

| Protein Name | Gene ORF Name[a] | Coccidioides isolate[b] [n[c]] |
|---|---|---|
| 40S ribosomal protein S14 | CIMG_04348/ CPSG_09614 | Ci RS [1] |
| 60S ribosomal protein L12 | CIMG_04811/ CPSG_07687 | Cp Sil [2] |
| Endochitinase 1 | CIMG_02795/ CPSG_08657 | Ci RS [1], Cp Sil [3] |
| Gamma-glutamyltranspeptidase | CIMG_05765/ CPSG_02828 | Cp Sil [2] |
| Peroxisomal matrix protein | CIMG_05828/ CPSG_04764 | Ci RS [2] |
| Serine protease | CIMG_10287/ CPSG_04717 | Ci 2006 [3], Ci RS [3], Cp Sil [2] |
| Triosephosphate isomerase | CIMG_09361/ CPSG_03911 | Ci 2006 [1], Ci RS [1], Cp Sil [1] |
| Uncharacterized protein | CIMG_09001/ CPSG_01366 | Ci 2006 [2], Ci RS [1], Cp Sil [3] |

[a]Listing of Gene Open Reading Frame (ORF) name for orthologous loci in both species in this arrangement: *C. immitis* isolate RS/*C. posadasii* isolate Silveira
[b]Ci 2006: *C. immitis* isolate 2006, Ci RS: *C. immitis* isolate RS, Cp Sil: *C. posadasii* Silveria
[c]Number of mice per infection group in which this protein was identified.

Three proteins shown in TABLE 7, a *Coccidioides* serine protease (CIMG_10287/CPSG_04717), a triosephosphate isomerase (CIMG_09361/CPSG_03911), and an uncharacterized protein (CIMG_09001/CPSG_01366) were identified in the BALFs collected from all infection groups. The *Coccidioides* serine protease identified in all of the mouse infection groups is a member of an expanded subtilisin N domain-containing extracellular serine protease family in *Coccidioides* implicated in host interactions but is currently uncharacterized (see Reference 38). Orthologous serine proteases have been shown to be virulence factors expressed during infection by other human pathogenic fungal and bacterial species (see Reference 38).

Other *Coccidioides* proteins were found in only one or two infection groups. As an example, endochitinase 1 (CIMG_02795/CPSG_08657) was identified from one mouse infected with RS and all three of the mice infected with Silveira. It is a member of a well-characterized family of chitinase proteins in *Coccidioides* that have been shown to be up-regulated during the parasitic life cycle (39, 40). CTS1 is also immunogenic and is used as a serodiagnostic antigen for disease (see Reference 41).

A peroxisomal matrix protein (PMP1) (CIMG_05828/CPSG_04764) was identified in two of the mice infected with RS. A recombinant PMP1 was found previously to be reactive with serum from individuals with both acute and protracted coccidioidomycosis (see Reference 42). The potential of this protein as a recombinant vaccine candidate was also examined, and evoked protection in two murine models of infection with *C. posadasii* (see Reference 42). Thus, the present approach was validated by the identification of previously characterized *Coccidioides* proteins that are known to be associated with the parasitic life cycle.

It is to be understood that unless specifically stated otherwise, references to "a," "an," and/or "the" may include one or more than one and that reference to an item in the singular may also include the item in the plural. Reference to an element by the indefinite article "a," "an" and/or "the" does not exclude the possibility that more than one of the elements are present, unless the context clearly requires that there is one and only one of the elements. As used herein, the term "comprise," and conjugations or any other variation thereof, are used in its non-limiting sense to mean that items following the word are included, but items not specifically mentioned are not excluded.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

REFERENCES

The publications discussed herein are provided solely for their disclosure prior to the filing date of the present application. Nothing herein is to be construed as an admission that the present invention is not entitled to antedate such publication by virtue of prior invention.

1. Lewis E R, Bowers J R, Barker B M. 2015. Dust devil: the life and times of the fungus that causes valley Fever. PLoS Pathog 11:e1004762.

2. Brown J, Benedict K, Park B J, Thompson G R, 3rd. 2013. Coccidioidomycosis: epidemiology. Clin Epidemiol 5:185-197.

3. Nguyen C, Barker B M, Hoover S, Nix D E, Ampel N M, Frelinger J A, Orbach M J, Galgiani J N. 2013. Recent advances in our understanding of the environmental, epidemiological, immunological, and clinical dimensions of coccidioidomycosis. Clin Microbiol Rev 26:505-525.

4. Nesbit L A, Knox K S, Nguyen C T, Roesch J, Wheat L J, Johnson S M, Pappagianis D, Chavez S, Ampel N M. 2013 Immunological characterization of bronchoalveolar lavage fluid in patients with acute pulmonary coccidioidomycosis. J Infect Dis 208:857-863.

5. Ampel N M, Dionne S O, Giblin A, Podany A B, Galgiani J. 2009. Mannose-binding lectin serum levels are low in persons with clinically active coccidioidomycosis. Mycopathologia 167:173-180.

6. Cox R A, Kennell W, Boncyk L, Murphy J W. 1988. Induction and expression of cell-mediated immune responses in inbred mice infected with *Coccidioides immitis*. Infect Immun 56:13-17.

7. Magee D M, Cox R A. 1995. Roles of gamma interferon and interleukin-4 in genetically determined resistance to *Coccidioides immitis*. Infect Immun 63:3514-3519.

8. Fierer J, Walls L, Eckmann L, Yamamoto T, Kirkland T N. 1998. Importance of interleukin-10 in genetic susceptibility of mice to *Coccidioides immitis*. Infect Immun 66:4397-4402.

9. Cain J A, Deepe G S, Jr. 1998. Evolution of the primary immune response to *Histoplasma capsulatum* in murine lung. Infect Immun 66:1473-1481.

10. Zhou P, Sieve M C, Bennett J, Kwon-Chung K J, Tewari R P, Gazzinelli R T, Sher A, Seder R A. 1995. IL-12 prevents mortality in mice infected with *Histoplasma capsulatum* through induction of IFN-gamma. J Immunol 155: 785-795.

11. Gonzalez A, Sahaza J H, Ortiz B L, Restrepo A, Cano L E. 2003. Production of pro-inflammatory cytokines during the early stages of experimental *Paracoccidioides brasiliensis* infection. Med Mycol 41:391-399.

12. Schelenz S, Smith D A, Bancroft G J. 1999. Cytokine and chemokine responses following pulmonary challenge with *Aspergillus fumigatus*: obligatory role of TNF-alpha and GM-CSF in neutrophil recruitment. Med Mycol 37:183-194.

13. Caffrey A K, Lehmann M M, Zickovich J M, Espinosa V, Shepardson K M, Watschke C P, Hilmer K M, Thammahong A, Barker B M, Rivera A, Cramer R A, Obar J J. 2015. IL-1alpha signaling is critical for leukocyte recruitment after pulmonary *Aspergillus fumigatus* challenge. PLoS Pathog 11:e1004625.

14. Murdock B J, Huffnagle G B, Olszewski M A, Osterholzer J J. 2014. Interleukin-17A enhances host defense against cryptococcal lung infection through effects mediated by leukocyte recruitment, activation, and gamma interferon production. Infect Immun 82:937-948.

15. Burt A, Dechairo B M, Koenig G L, Carter D A, White T J, Taylor J W. 1997. Molecular markers reveal differentiation among isolates of *Coccidioides immitis* from California, Arizona and Texas. Mol Ecol 6:781-786.

16. Fisher M C, Koenig G L, White T J, Taylor J W. 2002. Molecular and phenotypic description of *Coccidioides posadasii* sp. nov., previously recognized as the non-California population of *Coccidioides immitis*. Mycologia 94:73-84.

17. Friedman L, Smith C E, Gordon L E. 1955. The assay of virulence of *Coccidioides* in white mice. J Infect Dis 97:311-316.

18. Zimmermann C R, Snedker C J, Pappagianis D. 1994. Characterization of *Coccidioides immitis* isolates by restriction fragment length polymorphisms. J Clin Microbiol 32:3040-3042.

19. Shubitz L F, Dial S M, Perrill R, Casement R, Galgiani J N. 2008. Vaccine-induced cellular immune responses differ from innate responses in susceptible and resistant strains of mice infected with *Coccidioides posadasii*. Infect Immun 76:5553-5564.

20. Chung D, Barker B M, Carey C C, Merriman B, Werner E R, Lechner B E, Dhingra S, Cheng C, Xu W, Blosser S J, Morohashi K, Mazurie A, Mitchell T K, Haas H, Mitchell A P, Cramer R A. 2014. ChIP-seq and in vivo transcriptome analyses of the *Aspergillus fumigatus* SREBP SrbA reveals a new regulator of the fungal hypoxia response and virulence. PLoS Pathog 10:e1004487.

21. Livak K J, Schmittgen T D. 2001. Analysis of relative gene expression data using real-time quantitative PCR and the 2(-Delta Delta C(T)) Method. Methods 25:402-408.

22. Shevchenko A, Tomas H, Havlis J, Olsen J V, Mann M. 2006. In-gel digestion for mass spectrometric characterization of proteins and proteomes. Nat Protoc 1:2856-2860.

23. Keller A, Nesvizhskii A I, Kolker E, Aebersold R. 2002. Empirical statistical model to estimate the accuracy of peptide identifications made by MS/MS and database search. Anal Chem 74:5383-5392.

24. Bindea G, Mlecnik B, Hackl H, Charoentong P, Tosolini M, Kirilovsky A, Fridman W H, Pages F, Trajanoski Z, Galon J. 2009. ClueGO: a Cytoscape plug-in to decipher functionally grouped gene ontology and pathway annotation networks. Bioinformatics 25:1091-1093.

25. Chen J, Bardes E E, Aronow B J, Jegga A G. 2009. ToppGene Suite for gene list enrichment analysis and candidate gene prioritization. Nucleic Acids Res 37:W305-311.

26. Cuervo A M, Gomes A V, Barnes J A, Dice J F. 2000. Selective degradation of annexins by chaperone-mediated autophagy. J Biol Chem 275:33329-33335.

27. Cowburn A S, Sobolewski A, Reed B J, Deighton J, Murray J, Cadwallader K A, Bradley J R, Chilvers E R. 2006. Aminopeptidase N (CD13) regulates tumor necrosis factor-alpha-induced apoptosis in human neutrophils. J Biol Chem 281:12458-12467.

28. Scharfstein J. 2006. Parasite cysteine proteinase interactions with alpha 2-macroglobulin or kininogens: differential pathways modulating inflammation and innate immunity in infection by pathogenic trypanosomatids. Immunobiology 211:117-125.

29. Merle N S, Noe R, Halbwachs-Mecarelli L, Fremeaux-Bacchi V, Roumenina L T. 2015. Complement System Part II: Role in Immunity. Front Immunol 6:257.

30. Dutra F F, Bozza M T. 2014. Heme on innate immunity and inflammation. Front Pharmacol 5:115.

31. Vadasz I, Weiss C H, Sznajder J I. 2012. Ubiquitination and proteolysis in acute lung injury. Chest 141:763-771.

32. Crosby L M, Waters C M. 2010. Epithelial repair mechanisms in the lung. Am J Physiol Lung Cell Mol Physiol 298:L715-731.

33. McAleer J P, Kolls J K. 2014. Directing traffic: IL-17 and IL-22 coordinate pulmonary immune defense. Immunol Rev 260:129-144.

34. Parker D, Prince A. 2011. Innate immunity in the respiratory epithelium. Am J Respir Cell Mol Biol 45:189-201.

35. Tang X X, Fok K L, Chen H, Chan K S, Tsang L L, Rowlands D K, Zhang X H, Dong J D, Ruan Y C, Jiang X, Yu S S, Chung Y W, Chan H C. 2012. Lymphocyte CFTR promotes epithelial bicarbonate secretion for bacterial killing. J Cell Physiol 227:3887-3894.

36. Christin L, Wysong D R, Meshulam T, Hastey R, Simons E R, Diamond R D. 1998. Human platelets damage *Aspergillus fumigatus* hyphae and may supplement killing by neutrophils. Infect Immun 66:1181-1189.

37. Yeaman M R. 2010. Bacterial-platelet interactions: virulence meets host defense. Future Microbiol 5:471-506.

38. Sharpton T J, Stajich J E, Rounsley S D, Gardner M J, Wortman J R, Jordar V S, Maiti R, Kodira C D, Neafsey D E, Zeng Q, Hung C Y, McMahan C, Muszewska A, Grynberg M, Mandel M A, Kellner E M, Barker B M, Galgiani J N, Orbach M J, Kirkland T N, Cole G T, Henn M R, Birren B W, Taylor J W. 2009. Comparative genomic analyses of the human fungal pathogens *Coccidioides* and their relatives. Genome Res 19:1722-1731.

39. Pishko E J, Kirkland T N, Cole G T. 1995. Isolation and characterization of two chitinase-encoding genes (cts1, cts2) from the fungus *Coccidioides immitis*. Gene 167:173-177.

40. Whiston E, Zhang Wise H, Sharpton T J, Jui G, Cole G T, Taylor J W. 2012. Comparative transcriptomics of the saprobic and parasitic growth phases in *Coccidioides* spp. PLoS One 7:e41034.

41. Johnson S M, Pappagianis D. 1992. The coccidioidal complement fixation and immunodiffusion-complement fixation antigen is a chitinase. Infect Immun 60:2588-2592.

42. Orsborn K I, Shubitz L F, Peng T, Kellner E M, Orbach M J, Haynes P A, Galgiani J N. 2006. Protein expression profiling of *Coccidioides posadasii* by two-dimensional differential in-gel electrophoresis and evaluation of a newly recognized peroxisomal matrix protein as a recombinant vaccine candidate. Infect Immun 74:1865-1872.

43. Sobonya R E, Yanes J, Klotz S A. 2014. Cavitary pulmonary coccidioidomycosis: pathologic and clinical correlates of disease. Hum Pathol 45:153-159.

44. Cox R A, Magee D M. 2004. Coccidioidomycosis: host response and vaccine development. Clin Microbiol Rev 17:804-839, table of contents.

45. Check I J, Kidd M R, Staton G W, Jr. 1986. Systemic and lung protein changes in sarcoidosis. Lymphocyte counts, gallium uptake values, and serum angiotensin-converting enzyme levels may reflect different aspects of disease activity. Ann N Y Acad Sci 465:407-417.

46. Atochina E N, Beck J M, Preston A M, Haczku A, Tomer Y, Scanlon S T, Fusaro T, Casey J, Hawgood S, Gow A J, Beers M F. 2004. Enhanced lung injury and delayed clearance of *Pneumocystis carinii* in surfactant protein A-deficient mice: attenuation of cytokine responses and reactive oxygen-nitrogen species. Infect Immun 72:6002-6011.

47. Jin W, Rong L, Liu Y, Song Y, Li Y, Pan J. 2013. Increased claudin-3, -4 and -18 levels in bronchoalveolar lavage fluid reflect severity of acute lung injury. Respirology 18:643-651.

48. Muhammed M, Feldmesser M, Shubitz L F, Lionakis M S, Sil A, Wang Y, Glavis-Bloom J, Lewis R E, Galgiani J N, Casadevall A, Kontoyiannis D P, Mylonakis E. 2012. Mouse models for the study of fungal pneumonia: a collection of detailed experimental protocols for the study of *Coccidioides, Cryptococcus, Fusarium, Histoplasma* and combined infection due to *Aspergillus-Rhizopus*. Virulence 3:329-338.

49. Dixon D M, Polak A, Walsh T J. 1989. Fungus dose-dependent primary pulmonary aspergillosis in immunosuppressed mice. Infect Immun 57:1452-1456.

50. Sawyer R T. 1990. Experimental pulmonary candidiasis. Mycopathologia 109:99-109.

51. Wormley F L, Jr., Perfect J R, Steele C, Cox G M. 2007. Protection against cryptococcosis by using a murine gamma interferon-producing *Cryptococcus neoformans* strain. Infect Immun 75:1453-1462.

52. Nicas M, Hubbard A. 2002. A risk analysis for airborne pathogens with low infectious doses: application to respirator selection against *Coccidioides immitis* spores. Risk Anal 22:1153-1163.

53. Cox R A. 1988 Immunosuppression by cell wall antigens of *Coccidioides immitis*. Rev Infect Dis 10 Suppl 2:S415-418.

54. Cox R A, Kennell W. 1988. Suppression of T-lymphocyte response by *Coccidioides immitis* antigen. Infect Immun 56:1424-1429.

55. Hung C Y, Ampel N M, Christian L, Seshan K R, Cole G T. 2000. A major cell surface antigen of *Coccidioides immitis* which elicits both humoral and cellular immune responses. Infect Immun 68:584-593.

56. Hung C Y, Yu J J, Seshan K R, Reichard U, Cole G T. 2002. A parasitic phase-specific adhesin of *Coccidioides immitis* contributes to the virulence of this respiratory fungal pathogen. Infect Immun 70:3443-3456.

57. Hung C Y, Seshan K R, Yu J J, Schaller R, Xue J, Basrur V, Gardner M J, Cole G T. 2005. A metalloproteinase of *Coccidioides posadasii* contributes to evasion of host detection. Infect Immun 73:6689-6703.

58. Johannesson H, Townsend J P, Hung C Y, Cole G T, Taylor J W. 2005. Concerted evolution in the repeats of an immunomodulating cell surface protein, SOWgp, of the human pathogenic fungi *Coccidioides immitis* and *C. posadasii*. Genetics 171:109-117.

59. Hung C Y, Xue J, Cole G T. 2007. Virulence mechanisms of *Coccidioides*. Ann N Y Acad Sci 1111:225-235.

60. Deitsch K W, Lukehart S A, Stringer J R. 2009. Common strategies for antigenic variation by bacterial, fungal and protozoan pathogens. Nat Rev Microbiol 7:493-503.

61. Chotirmall S H, Mirkovic B, Lavelle G M, McElvaney N G. 2014 Immunoevasive *Aspergillus* virulence factors. Mycopathologia 178:363-370.

62. Reddick L E, Alto N M. 2014. Bacteria fighting back: how pathogens target and subvert the host innate immune system. Mol Cell 54:321-328.

63. Neafsey D E, Barker B M, Sharpton T J, Stajich J E, Park D J, Whiston E, Hung C Y, McMahan C, White J, Sykes S, Heiman D, Young S, Zeng Q, Abouelleil A, Aftuck L, Bessette D, Brown A, FitzGerald M, Lui A, Macdonald J P, Priest M, Orbach M J, Galgiani J N, Kirkland T N, Cole G T, Birren B W, Henn M R, Taylor J W, Rounsley S D. 2010. Population genomic sequencing of *Coccidioides* fungi reveals recent hybridization and transposon control. Genome Res 20:938-946.

What is claimed is:

1. A method of detecting a fungal infection caused by *Coccidioides*, the method comprising the steps of:

obtaining a sample from a subject suspected of having the fungal infection; and detecting a *Coccidioides* protein having the amino acid sequence of SEQ ID NO: 3 in the sample, wherein a presence of the *Coccidioides* protein indicates a presence of the fungal infection caused by *Coccidioides*.

2. The method of claim 1, wherein the *Coccidioides* protein having the amino acid sequence of SEQ ID NO: 3 is detected using liquid chromatography.

3. The method of claim 1, wherein the *Coccidioides* protein is detected using an antibody capable of binding to the amino acid sequence of SEQ ID NO: 3.

4. The method of claim 1, wherein the sample is a pulmonary sample.

5. The method of claim 1, wherein the sample is obtained within one week of the subject being exposed to the fungal infection.

6. The method of claim 1, further comprising the step of:

augmenting an expression level of the *Coccidioides* protein.

7. A method of detecting a fungal infection caused by *Coccidioides* in a subject, comprising:

receiving a sample from the subject;

adding to a mixture comprising the sample a reagent capable of binding to a marker, wherein the marker comprises the amino acid sequence of SEQ ID NO: 3;

subjecting the mixture to conditions that allow detection of binding of the reagent to the marker;

assessing an expression of the marker in the sample; and determining a presence or absence of the fungal infection based on the expression of the marker.

8. The method of claim 7, wherein the reagent comprises an antibody capable of binding to the amino acid sequence of SEQ ID NO: 3.

9. The method of claim 7, wherein assessing an expression of the marker further comprises:

assessing the expression level of the marker in the sample and a control sample, by determining a level of binding of the reagent to the marker in the sample and determining a level of binding to the marker in the control sample; and detecting the presence of the fungal infection when the expression level of the marker in the sample is greater than the expression level of the marker in the control sample.

10. The method of claim 9, wherein the control sample is derived from a subject that does not have the fungal infection.

11. The method of claim 7, wherein the sample is a pulmonary sample.

* * * * *

UNITED STATES PATENT AND TRADEMARK OFFICE
CERTIFICATE OF CORRECTION

| | |
|---|---|
| PATENT NO. | : 10,401,359 B2 |
| APPLICATION NO. | : 15/677009 |
| DATED | : September 3, 2019 |
| INVENTOR(S) | : Bridget M. Barker and Patrick Pirrotte |

It is certified that error appears in the above-identified patent and that said Letters Patent is hereby corrected as shown below:

In the Specification

Column 1, Lines 15-18, cancel the text "This invention was made with government support under K22 AI104801 awarded by the National Institute of Allergy and Infectious Diseases. The government has certain rights in this invention.", and insert the following text:

--This invention was made with government support under Grant Number AI104801, awarded by the National Institutes of Health. The government has certain rights in the invention.--

Signed and Sealed this
Eighteenth Day of April, 2023

Katherine Kelly Vidal
*Director of the United States Patent and Trademark Office*